United States Patent
Shigeta

(10) Patent No.: US 11,426,054 B2
(45) Date of Patent: Aug. 30, 2022

(54) MEDICAL IMAGE PROCESSING SYSTEM, ENDOSCOPE SYSTEM, DIAGNOSIS SUPPORT APPARATUS, AND MEDICAL SERVICE SUPPORT APPARATUS

(71) Applicant: FUJIFILM Corporation, Tokyo (JP)

(72) Inventor: Norimasa Shigeta, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/847,679

(22) Filed: Apr. 14, 2020

(65) Prior Publication Data

US 2020/0237184 A1 Jul. 30, 2020

Related U.S. Application Data

(63) Continuation of application No. PCT/JP2018/038624, filed on Oct. 17, 2018.

(30) Foreign Application Priority Data

Oct. 18, 2017 (JP) .............................. JP2017-201490

(51) Int. Cl.
*A61B 1/00* (2006.01)
*A61B 1/005* (2006.01)
*A61B 1/06* (2006.01)

(52) U.S. Cl.
CPC ........ *A61B 1/00009* (2013.01); *A61B 1/0005* (2013.01); *A61B 1/00055* (2013.01);
(Continued)

(58) Field of Classification Search
CPC .............. A61B 1/00009; A61B 1/0005; A61B 1/00055; A61B 1/00186; A61B 1/00188;
(Continued)

(56) References Cited

U.S. PATENT DOCUMENTS 7,641,609 B2 * 1/2010 Ohnishi ............... A61B 1/0005
600/117
9,773,185 B2 9/2017 Kanda
(Continued)

FOREIGN PATENT DOCUMENTS

JP H06181885 7/1994
JP 2006198106 8/2006
(Continued)

OTHER PUBLICATIONS

"Office Action of Japan Counterpart Application", dated Apr. 27, 2021, with English translation thereof, p. 1-p. 8.
(Continued)

*Primary Examiner* — Timothy J Neal
*Assistant Examiner* — Sung Ham
(74) *Attorney, Agent, or Firm* — JCIPRNET

(57) ABSTRACT

A region-of-interest detection unit detects the region of interest including the target of interest among an observation target, from the medical image. An overlooking determination unit determines whether a user overlooks the target of interest. A monitor includes a first screen which displays a video of the medical image and displays the region of interest, and a second screen which is a screen different from the first screen and displays the region of interest. An overlooking notification control unit performs a control of an overlooking occurrence notification in a case where it is determined that the target of interest is overlooked.

14 Claims, 18 Drawing Sheets

(52) U.S. Cl.
CPC ......... *A61B 1/0051* (2013.01); *A61B 1/00186* (2013.01); *A61B 1/00188* (2013.01); *A61B 1/0638* (2013.01)

(58) Field of Classification Search
CPC ..... A61B 1/0051; A61B 1/0638; A61B 1/043; A61B 1/00039; A61B 1/00045; A61B 1/00163; A61B 1/041; G01N 21/64; G01N 21/6456; G01N 21/6486; G06T 7/0016; G06T 7/0028
USPC .................................. 382/128; 600/101, 476
See application file for complete search history.

(56) References Cited

U.S. PATENT DOCUMENTS

| | | | |
|---|---|---|---|
| 9,888,831 B2 | 2/2018 | Yoshino | |
| 10,918,265 B2 | 2/2021 | Watanabe et al. | |
| 2008/0009669 A1 | 1/2008 | Ozawa et al. | |
| 2009/0135202 A1* | 5/2009 | Keuenhof | G06F 3/1446 345/629 |
| 2009/0292175 A1* | 11/2009 | Akimoto | A61B 1/2676 600/156 |
| 2011/0221756 A1* | 9/2011 | Inoue | A61B 5/1075 345/501 |
| 2012/0033866 A1* | 2/2012 | Masumoto | G06T 19/00 382/128 |
| 2012/0274754 A1 | 11/2012 | Tsuruoka | |
| 2013/0114904 A1* | 5/2013 | Chang | G06T 7/174 382/203 |
| 2014/0184790 A1 | 7/2014 | Ishihara | |
| 2016/0093046 A1* | 3/2016 | Jeon | G06T 7/20 382/128 |
| 2016/0148053 A1* | 5/2016 | Matsuzaki | G06K 9/00711 382/128 |
| 2016/0163106 A1* | 6/2016 | Serlie | G06T 19/00 382/128 |
| 2016/0296106 A1* | 10/2016 | Shoji | A61B 1/0638 |
| 2018/0110491 A1* | 4/2018 | Ishida | A61B 6/5217 |
| 2018/0206738 A1 | 7/2018 | Kamon | |
| 2018/0242817 A1* | 8/2018 | Imaizumi | G06T 7/0012 |
| 2018/0249900 A1* | 9/2018 | Imaizumi | A61B 1/00009 |
| 2018/0307933 A1* | 10/2018 | Iwaki | A61B 1/04 |
| 2019/0069757 A1* | 3/2019 | Iwaki | A61B 1/0005 |
| 2020/0058124 A1* | 2/2020 | Iwaki | A61B 1/00045 |
| 2020/0065970 A1* | 2/2020 | Sonoda | G06T 7/70 |
| 2020/0129042 A1* | 4/2020 | Takahashi | A61B 1/0005 |
| 2021/0113161 A1* | 4/2021 | Fukushima | A61B 8/463 |

FOREIGN PATENT DOCUMENTS

| | | | |
|---|---|---|---|
| JP | 2010035756 | | 2/2010 |
| JP | 2010035756 A | * | 2/2010 |
| JP | 2010172673 | | 8/2010 |
| JP | 4751593 | | 8/2011 |
| JP | 2011160848 | | 8/2011 |
| JP | 2011255006 | | 12/2011 |
| JP | 2011255006 A | * | 12/2011 |
| JP | 2012222658 | | 11/2012 |
| JP | 2013030105 | | 2/2013 |
| JP | 2013056040 | | 3/2013 |
| JP | 2015032127 | | 2/2015 |
| JP | 2017070504 | | 4/2017 |
| WO | 2016006284 | | 1/2016 |
| WO | 2017073337 | | 5/2017 |
| WO | 2017081976 | | 5/2017 |
| WO | 2017110459 | | 6/2017 |

OTHER PUBLICATIONS

"International Search Report (Form PCT/ISA/210) of PCT/JP2018/038624," dated Jan. 15, 2019, with English translation thereof, pp. 1-5.

"Written Opinion of the International Searching Authority (Form PCT/ISA/237) of PCT/JP2018/038624," dated Jan. 15, 2019, with English translation thereof, pp. 1-12.

"Office Action of Japan Counterpart Application" with English translation thereof, dated Nov. 30, 2021, p. 1-p. 10.

"Office Action of Japan Counterpart Application" with English translation thereof, dated Jun. 7, 2022, p. 1-p. 7.

* cited by examiner

MEDICAL IMAGE PROCESSING SYSTEM, ENDOSCOPE SYSTEM, DIAGNOSIS SUPPORT APPARATUS, AND MEDICAL SERVICE SUPPORT APPARATUS

CROSS-REFERENCE TO RELATED APPLICATIONS

This application is a Continuation of PCT International Application No. PCT/JP2018/038624 filed on 17 Oct. 2018, which claims priority under 35 U.S.C § 119(a) to Japanese Patent Application No. 2017-201490 filed on 18 Oct. 2017. The above application is hereby expressly incorporated by reference, in its entirety, into the present application.

BACKGROUND OF THE INVENTION

1. Field of the Invention

The present invention relates to a medical image processing system, an endoscope system, a diagnosis support apparatus, and a medical service support apparatus which detect a region of interest from a medical image.

2. Description of the Related Art

In the current medical field, a medical image processing device using a medical image, such as a processor device for an endoscope incorporated in an endoscope system is widespread. In recent years, acquiring diagnosis support information relating to a disease state by detecting a region of interest having a possibility of a lesion area from a medical image and performing image analysis on the detected region of interest has been performed. The acquired diagnosis support information is provided to a user by being displayed on a display unit such as a monitor.

In a case where detection of a region of interest is performed as described above, it is required not to overlook a target of interest included in the region of interest at a timing at which the region of interest is detected. For example, in JP4751593B, in a case where a region of interest is detected from a medical image, the fact that the region of interest is detected is notified to a user by a sound such as a notice sound, a notification sound, and an end sound. Further, in JP2010-035756A, in a case where a region of interest is detected from a medical image, the user's gaze is detected, a time during which the detected gaze is directed at the region of interest is calculated as an observation time, and whether there is an overlooked target of interest is determined on the basis of the calculated time.

In JP2010-172673A, in a case where a region of interest is detected from a medical image, the detection of the region of interest is notified by a message, a character, an icon, a pop-up, or the like in addition to a sound. Further, in JP2006-198106A (corresponding to US2008/0009669A1), in a case where a region of interest is detected from a medical image, the medical image is captured at a timing at which the region of interest is detected, and the medical image in which the region of interest is marked is displayed as a thumbnail.

SUMMARY OF THE INVENTION

At the time of observing an observation target using a medical image, a region of interest is detected, but no matter how careful the user is, the user may overlook a target of interest as in a case where the target of interest instantly disappears from a screen. For example, in case of the endoscope, when the moving speed of the endoscope is high, when the target of interest is hidden behind the folds and the like, or when the target of interest is displayed at an end portion of the screen, the target of interest may be displayed on the screen only for a moment and disappear instantly. Therefore, even in such a case, it is required that the user can reliably notice the target of interest without overlook the target of interest.

An object of the invention is to provide a medical image processing system, an endoscope system, a diagnosis support apparatus, and a medical service support apparatus which prevent overlooking of a target of interest included in a region of interest in a case where the region of interest is detected from a medical image.

A medical image processing system according to an aspect of the invention comprises an image acquisition unit, a region-of-interest detection unit, an overlooking determination unit, a display unit, and an overlooking notification control unit. The image acquisition unit acquires a medical image obtained by imaging an observation target. The region-of-interest detection unit detects a region of interest including a target of interest in the observation target, from the medical image. The overlooking determination unit determines whether a user overlooks the target of interest. The display unit has a first screen which displays a video of the medical image and displays the region of interest, and a second screen which is a screen different from the first screen and displays the region of interest. The overlooking notification control unit that performs a control relating to an overlooking occurrence notification of the target of interest in a case where it is determined that the target of interest is overlooked.

It is preferable that in the second screen, a static image of the medical image including the region of interest and the target of interest is displayed. It is preferable that in the second screen, a first alert for prompting the user to confirm the region of interest is displayed. It is preferable that a confirmation signal generation unit that generates a region-of-interest confirmation signal relating to confirmation of the region of interest is provided, and the display unit displays a second alert indicating that the confirmation of the region of interest by the user is completed in the second screen in a case where the region-of-interest confirmation signal is generated. A region determination instruction generation unit that generates a region determination instruction relating to whether the region of interest is correctly detected is provided. It is preferable that the display unit displays a third alert indicating that the region of interest is correctly detected, in the second screen in a case where an instruction indicating that the region of interest is correctly detected is generated as the region determination instruction, and displays a fourth alert indicating that the region of interest is erroneously detected, in the second screen in a case where an instruction indicating that the region of interest is erroneously detected is generated as the region determination instruction.

The display unit has a third screen which is a screen different from the first screen and the second screen and displays a list of a plurality of static images. It is preferable that in the third screen, any one of a first alert for prompting confirmation of the region of interest by the user, a second alert indicating that confirmation of the region of interest by the user is completed, a third alert indicating that the region of interest is correctly detected, or a fourth alert indicating that the region of interest is erroneously detected is displayed. The second screen is displayed at a timing at which the region of interest is detected.

It is preferable that the overlooking determination unit determines overlooking of the target of interest from the medical image or a detection result of the region of interest. It is preferable that a gaze detection unit that detects a user's gaze directed at the display unit is provided, and the overlooking determination unit determines overlooking of the target of interest on the basis of an observation time during which the gaze is directed at the region of interest, obtained by the gaze detection unit. It is preferable that the overlooking notification control unit performs a control of causing the display unit to display a message indicating occurrence of the overlooking, as the overlooking occurrence notification.

It is preferable that a same-target-of-interest determination unit that determines whether a first target of interest displayed in the first screen at a first timing and a second target of interest displayed in the first screen at a second timing different from the first timing are the same, and a display control unit that performs a control of displaying or not displaying the second target of interest in the first screen or the second screen as the region of interest on the basis of a determination result of the same-target-of-interest determination unit are provided. It is preferable that the display control unit does not display the second target of interest in the first screen or the second screen as the region of interest in a case where the first target of interest and the second target of interest are the same. It is preferable that the display unit displays the target of interest by assigning an ID number to the target of interest.

An endoscope system according to an aspect of the invention comprises an endoscope, an image acquisition unit, a region-of-interest detection unit, an overlooking determination unit, a display unit, and an overlooking notification control unit. The endoscope images an observation target. The image acquisition unit acquires a medical image obtained by imaging the observation target. The region-of-interest detection unit detects a region of interest including a target of interest in the observation target, from the medical image. The overlooking determination unit determines whether a user overlooks the target of interest. The display unit has a first screen which displays a video of the medical image and displays the region of interest, and a second screen which is a screen different from the first screen and displays the region of interest. The overlooking notification control unit performs a control of an overlooking occurrence notification in a case where it is determined that the target of interest is overlooked.

A diagnosis support apparatus according to an aspect of the invention includes the above-described medical image processing system. A medical service support apparatus according to an aspect of the invention includes the above-described medical image processing system.

According to the invention, it is possible to prevent overlooking of a target of interest included in a region of interest in a case where the region of interest is detected from a medical image.

DESCRIPTION OF THE PREFERRED EMBODIMENTS

First Embodiment

Figure 1:
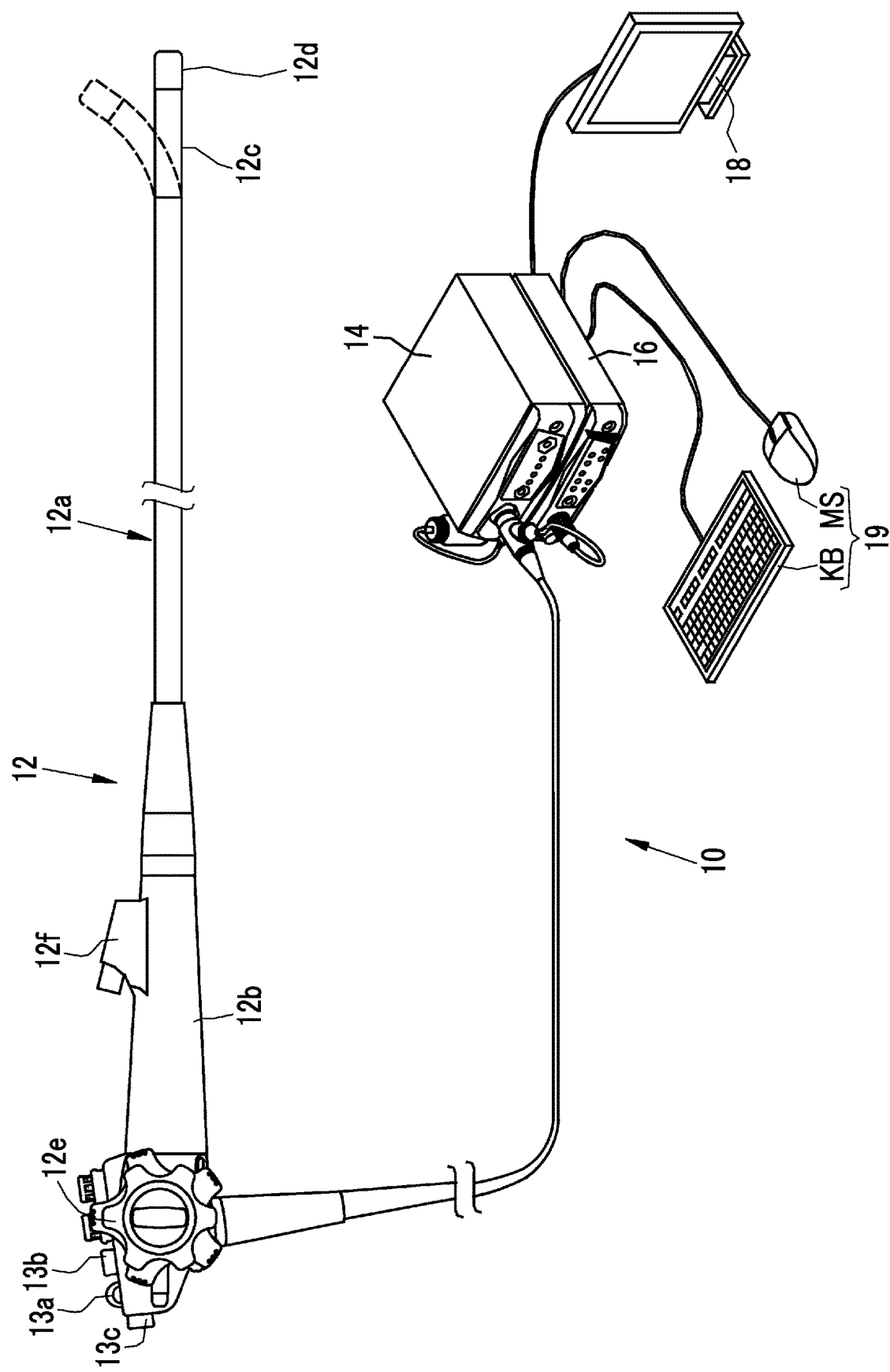
FIG. 1 is an external view of an endoscope system.

As illustrated in FIG. 1, an endoscope system 10 comprises an endoscope 12, a light source device 14, a processor device 16, a monitor 18, and a user interface 19. The endoscope 12 irradiates a subject as an observation target with illumination light, and images the subject irradiated with the illumination light. The light source device 14 generates illumination light to be emitted to the subject. The processor device 16 performs system control of the endoscope system 10, image processing, and the like. The monitor 18 is a display unit that displays an image output from the processor device 16. The user interface 19 is an input device for performing a setting input or the like with respect to the processor device 16 and the like, and is configured to include a keyboard KB, a mouse MS, and the like. The user interface 19 is not limited to the mouse MS and the keyboard KB, and may be a graphical user interface, a sound input, a touch display, or the like.

The endoscope 12 has an insertion part 12a that is to be inserted into an object to be examined, an operation part 12b provided in a proximal end portion of the insertion part 12a, and a bendable part 12c and a distal end part 12d that are provided on the distal end side of the insertion part 12a. The bendable part 12c is bent by operating an angle knob 12e of the operation part 12b. The distal end part 12d is directed in a desired direction by the bending of the bendable part 12c. A spray port (not illustrated) for spraying air, water, or the like toward the subject is provided in the distal end part 12d.

In addition to the angle knob 12e, a zoom operation part 13a is provided in the operation part 12b. The subject can be imaged in an enlarged or reduced manner by operating the zoom operation part 13a. Further, a freeze button 13b for acquiring a static image of a medical image is provided to the operation part 12b. The static image of the medical image obtained by the operation of the freeze button 13b is displayed on a static image list screen 76 (refer to FIG. 4) of the monitor 18 after an identification (ID) number is assigned to the static image. An ID number "1" is assigned to the static image acquired first, and thereafter, an ID number increased by "1" is assigned according to an acquisition order of the static images. A forceps channel (not illustrated) for inserting a treatment tool and the like is provided from the insertion part 12a to the distal end part 12d. The treatment tool is inserted into the forceps channel from a forceps inlet 12f.

Figure 2:
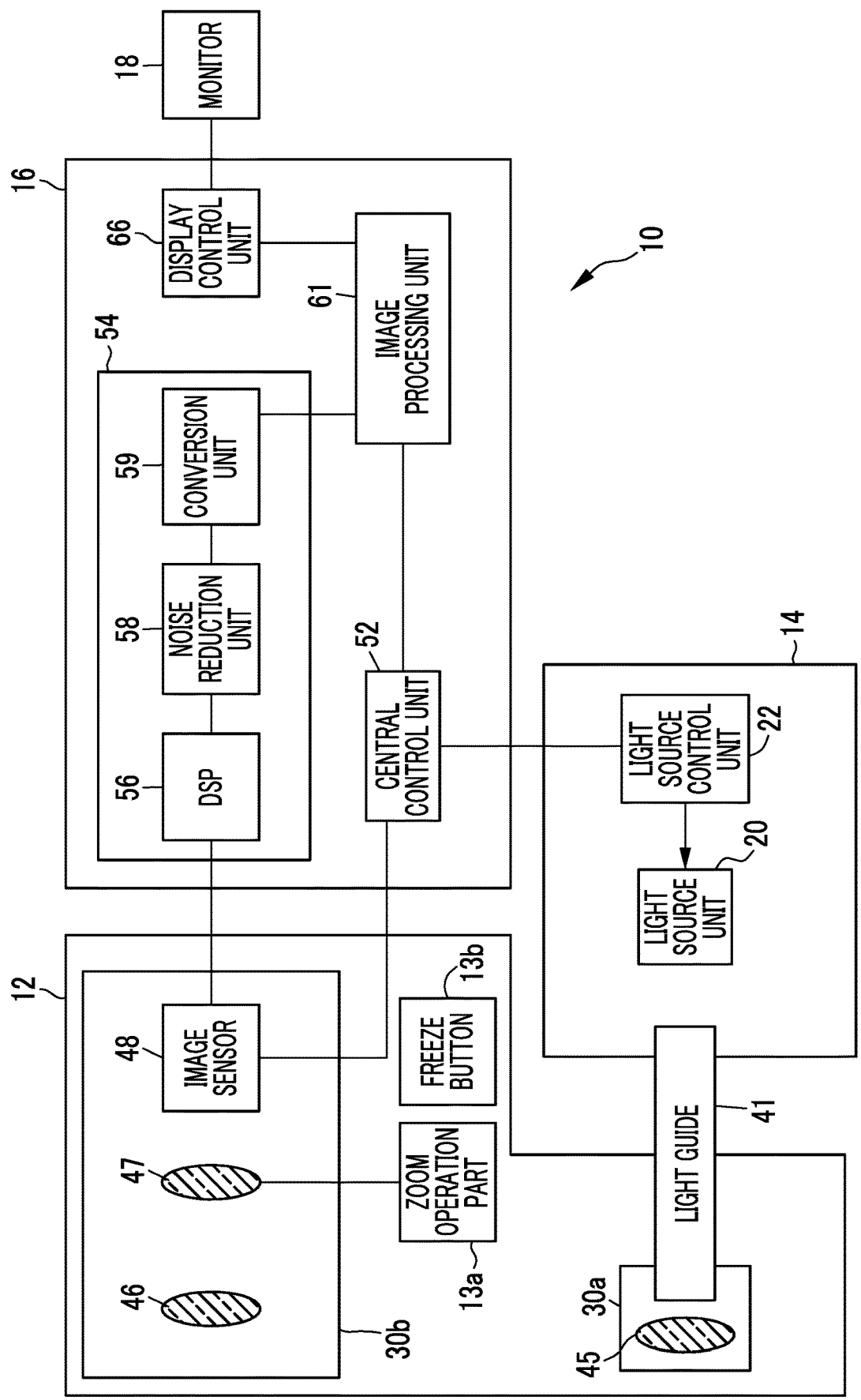
FIG. 2 is a block diagram of the endoscope system.

As illustrated in FIG. 2, the light source device 14 comprises a light source unit 20 and a light source control unit 22. The light source unit 20 emits illumination light for illuminating the subject. The light source unit 20 comprises one or a plurality of light sources. The light source control unit 22 controls the driving of the light source unit 20. The light source control unit 22 independently controls the timing of turning on or off the light sources constituting the light source unit 20, and the light emission amount or the like at the time of lighting. As a result, the light source unit 20 can emit a plurality of kinds of rays of illumination light with different light emission amounts and different light emission timings.

The illumination light emitted from the light source unit 20 is incident on a light guide 41. The light guide 41 is built in the endoscope 12 and a universal cord (not illustrated), and propagates illumination light to the distal end part 12d of the endoscope 12. The universal cord is a cord for connecting the endoscope 12 to the light source device 14 and the processor device 16. It is possible to use a multi-mode fiber as the light guide 41. As an example, it is possible to use a small-diameter fiber cable of which a core diameter is 105 μm, a cladding diameter is 125 μm, and a diameter including a protective layer as an outer skin is φ0.3 mm to φ0.5 mm.

An illumination optical system 30a and an imaging optical system 30b are provided in the distal end part 12d of the endoscope 12. The illumination optical system 30a has an illumination lens 45, and illumination light is emitted toward the subject through the illumination lens 45. The imaging optical system 30b has an objective lens 46, a zoom lens 47, and an image sensor 48. The image sensor 48 images the subject using reflected light or the like (including scattered light, fluorescence emitted from the subject, fluorescence due to medicine administered to the subject, and the like in addition to the reflected light) of the illumination light that returns from the subject through the objective lens 46 and the zoom lens 47. The zoom lens 47 is moved by operating the zoom operation part 13a, thereby enlarging or reducing the subject to be imaged by using the image sensor 48.

The image sensor 48 is, for example, a color sensor having primary color system color filters, and comprises three kinds of pixels of a blue pixel (B pixel) having a blue color filter, a green pixel (G pixel) having a green color filter, and a red pixel (R pixel) having a red color filter. The blue color filter mainly transmits violet to blue light. The green color filter mainly transmits green light. The red color filter mainly transmits red light. In a case where the subject is imaged using the primary color system image sensor 48 as described above, three types of images of a blue image (B image) obtained from the B pixel, a green image (G image) obtained from the G pixel, and a red image (R image) obtained from the R pixel can be simultaneously obtained at maximum.

As the image sensor 48, it is possible to use a charge coupled device (CCD) sensor or a complementary metal oxide semiconductor (CMOS) sensor. Although the image sensor 48 of the embodiment is a primary color system color sensor, it is also possible to use a complementary color system color sensor. For example, the complementary color system color sensor has a cyan pixel in which a cyan color filter is provided, a magenta pixel in which a magenta color filter is provided, a yellow pixel in which a yellow color filter is provided, and a green pixel in which a green color filter is provided. Images obtained from the pixels of the respective colors in case of using the complementary color system color sensor can be converted into the B image, the G image, and the R image by performing complementary color-primary color conversion. Instead of the color sensor, a monochrome sensor in which no color filter is provided can be used as the image sensor 48. In this case, it is possible to obtain images of the respective colors by sequentially imaging the subject using illumination light of respective colors such as BGR.

The processor device 16 includes a central control unit 52, an image acquisition unit 54, an image processing unit 61, and a display control unit 66. The central control unit 52 performs overall control of the endoscope system 10, such as synchronization control of irradiation timing of illumination light and imaging timing. In a case where various settings are input using the user interface 19 or the like, the central control unit 52 inputs the input various settings to each unit of the endoscope system 10, such as the light source control unit 22, the image sensor 48, or the image processing unit 61.

The image acquisition unit 54 acquires an image in which the subject is imaged, from the image sensor 48. Since the image acquired by the image acquisition unit 54 is an image obtained by a medical apparatus, such as the endoscope 12, the image is referred to as a medical image. The image acquisition unit 54 includes a digital signal processor (DSP) 56, a noise reduction unit 58, and a conversion unit 59, and performs various kinds of processing on the acquired medical image using these as necessary. The DSP 56 performs various kinds of processing, such as defect correction processing, offset processing, gain correction processing, linear matrix processing, gamma conversion processing, demosaicing processing, and YC conversion processing, on the acquired medical image as necessary.

The defect correction processing is processing for correcting the pixel value of each pixel corresponding to the defective pixel of the image sensor 48. The offset processing is processing for setting an accurate zero level by reducing a dark current component from the image subjected to the defect correction processing. The gain correction processing is processing for adjusting a signal level of each image by multiplying the image subjected to the offset processing by the gain. The linear matrix processing is processing for improving the color reproducibility of the image subjected to the offset processing, and the gamma conversion processing is processing for adjusting the brightness or the saturation of the image after the linear matrix processing.

In a case where the image sensor 48 is a color sensor, demosaicing processing is performed. The demosaicing processing (also referred to as isotropic processing or demosaicing) is processing for interpolating the pixel values of missing pixels, and is performed on the image after the gamma conversion processing. The missing pixel is a pixel having no pixel value due to the arrangement of color filters (since pixels of other colors are arranged in the image sensor 48). For example, since the B image is an image obtained by imaging the subject in the B pixel, a pixel at a position corresponding to the G pixel or the R pixel has no pixel value. The demosaicing processing is for generating the pixel values of pixels at the positions of the G and R pixels of the image sensor 48 by interpolating the B image. The YC conversion processing is processing for converting the image after the demosaicing processing into a luminance channel Y, a color difference channel Cb, and a color difference channel Cr.

The noise reduction unit 58 performs noise reduction processing on the luminance channel Y, the color difference channel Cb, and the color difference channel Cr using, for example, a moving average method or a median filter method. The conversion unit 59 reconverts the luminance channel Y, the color difference channel Cb, and the color difference channel Cr after the noise reduction processing into images of the respective colors of BGR.

Figure 3:
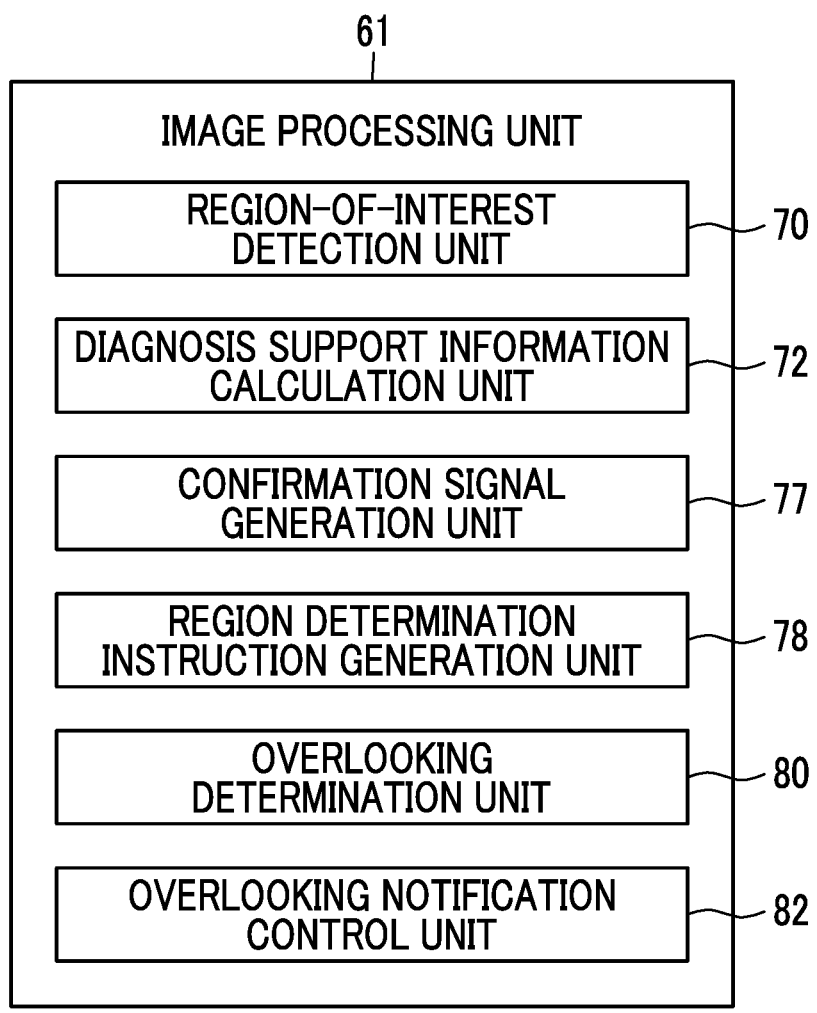
FIG. 3 is a block diagram illustrating a function of an image processing unit of a first embodiment.

As illustrated in FIG. 3, the image processing unit 61 comprises a region-of-interest detection unit 70, a diagnosis support information calculation unit 72, a confirmation signal generation unit 77, a region determination instruction generation unit 78, an overlooking determination unit 80, and an overlooking notification control unit 82. The region-of-interest detection unit 70 performs region detection processing for detecting a region of interest to be noticed as a target for inspection or diagnosis from the medical image. At the time of detecting the region of interest, the static image of the target of interest included in the region of interest is acquired together. The acquired static image of the target of interest is displayed on the static image list screen 76 (refer to FIG. 4, notation of "ID number" is omitted in drawings other than FIG. 4) after the ID number is assigned to the static image. The assignment of the ID number is similar to a case where the static image is acquired by the freeze button 13b.

The region-of-interest detection unit 70 is constituted by, for example, a convolutional neural network (CNN) or AdaBoost using pixel gradient features. Accordingly, the region-of-interest detection unit 70 can perform learning processing for increasing the detection accuracy of the region of interest in addition to the region detection processing. Whether to perform the region detection processing or the learning processing is determined by operating the user interface 19. In the region-of-interest detection unit 70, discrimination scores relating to the target of interest may be calculated together. The discrimination score is determined such that the discrimination score is increased as the probability that the target of interest is a target to be noted becomes higher.

The diagnosis support information calculation unit 72 calculates various index values from the region of interest detected by the region-of-interest detection unit 70, and calculates diagnosis support information for supporting diagnosis of a lesion area on the basis of the calculated various index values. As the various index values, a blood vessel index value relating to blood vessels such as a blood vessel density or a blood vessel running pattern, or a gland duct index value relating to gland duct structures are included. As the diagnosis support information, a progress degree (stage) of a lesion area or the like is exemplified.

Figure 4:
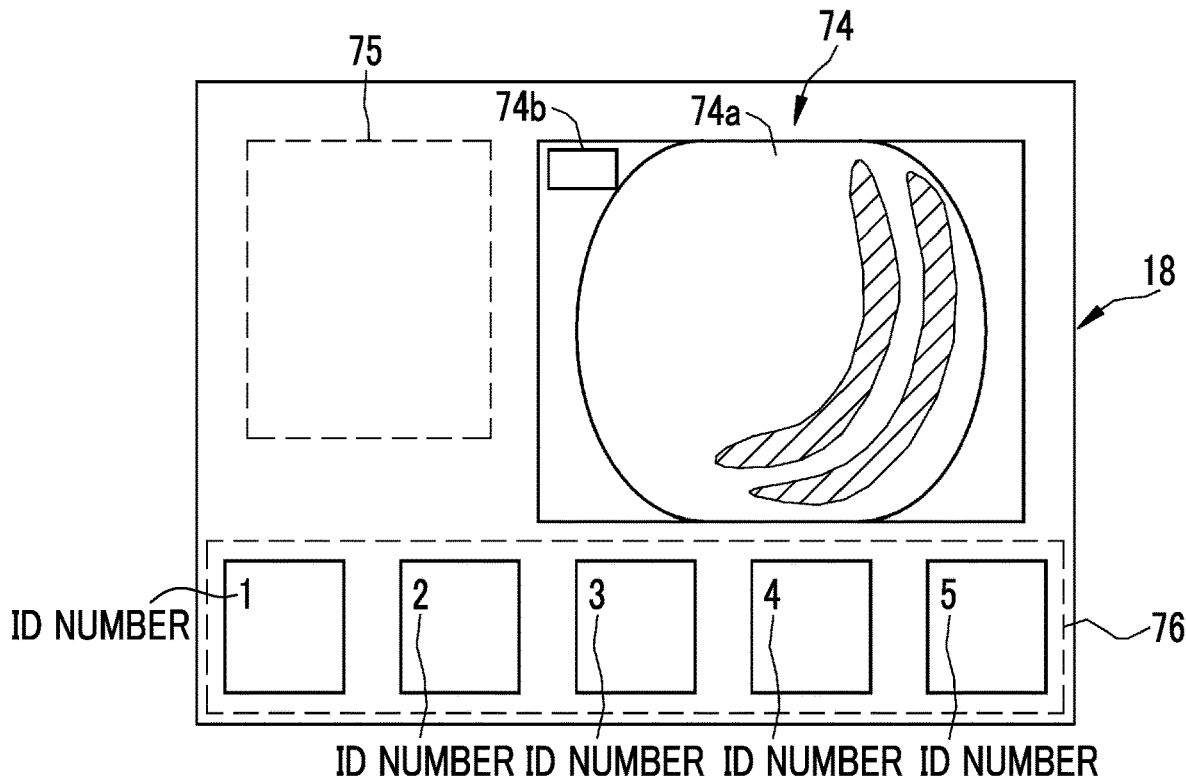
FIG. 4 is an image diagram of a monitor including a main screen, a sub screen, and a static image list screen.

The display control unit 66 converts the medical image transmitted from the image processing unit 61 or the diagnosis support information into a format suitable for display on the monitor 18, and outputs the conversion result to the monitor 18. In this manner, the medical image and the diagnosis support information are at least displayed on the monitor 18. As illustrated in FIG. 4, on the monitor 18, a main screen 74 (first screen) which displays a video of the medical image, a sub screen 75 (second screen) which displays the region of interest and the target of interest at the timing at which the region of interest is detected, and the static image list screen 76 (third screen) which displays static images obtained by the user's operation on the freeze button 13b or static images obtained at the timing at which the region of interest is detected by the region-of-interest detection unit 70 in a chronological order are displayed.

Figure 5:
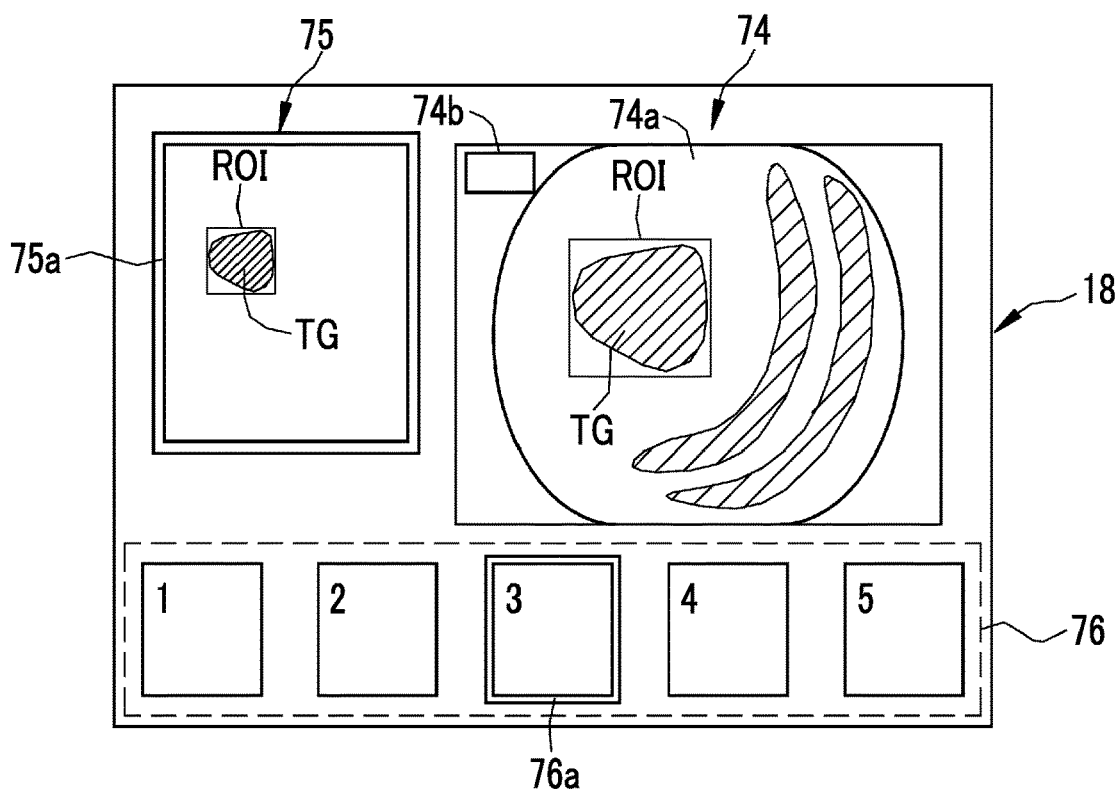
FIG. 5 is an image diagram of the monitor in a case where a region of interest is detected.

In the main screen 74, a medical image display unit 74a which is provided in the center of the screen and displays the video of the medical image, and a diagnosis support information display unit 74b which is provided in a side of the screen and displays the diagnosis support information. The sub screen 75 is not displayed on the monitor 18 (in FIG. 4, the sub screen 75 is indicated by a dotted line indicating non-display) in a case where there is no detection of the region of interest by the region-of-interest detection unit 70). In a case where the region of interest is detected by the region-of-interest detection unit 70, the sub screen 75 is displayed as illustrated in FIG. 5.

In the sub screen 75, the static image of the medical image including a region of interest ROI and a target of interest TG included in the region of interest ROI is displayed. It is preferable that the static image displayed in the sub screen 75 is a specific representative picture among the medical images obtained at the time of detection of the region of interest ROI. Further, a frame 75a of the sub screen 75 is displayed in a first color (for example, "red color") as an alert (first alert) for prompting the user to confirm the detection of the region of interest ROI. In FIG. 5, the shape of the region of interest ROI is indicated in a square (rectangle), but may be indicated in a shape other than the rectangle, such as a circle or an ellipse. Further, it is preferable that the static image in the sub screen 75 is updated to a static image having the highest discrimination score each time the region of interest is detected. Further, it is preferable that the static image in the sub screen 75 is updated at a certain time interval in case of performing observation with the distal end part 12d of the endoscope 12 stopped.

At the time of the detection of the region of interest ROI, the region of interest ROI and the target of interest TG are displayed together also in the main screen 74. Also in the static image list screen 76, the static image of the target of interest TG is displayed and a frame 76a of the screen of the static image is displayed in the same first color as the color of the frame of the sub screen. In a case where the region of interest ROI is detected, the "detection of the region of interest" may be notified by displaying an icon such as an arrow on the monitor 18 in addition to a sound, vibration (vibrating the operation part 12b of the endoscope), and change of illumination light (change from white light to blue monochromatic light, or the like).

Figure 6:
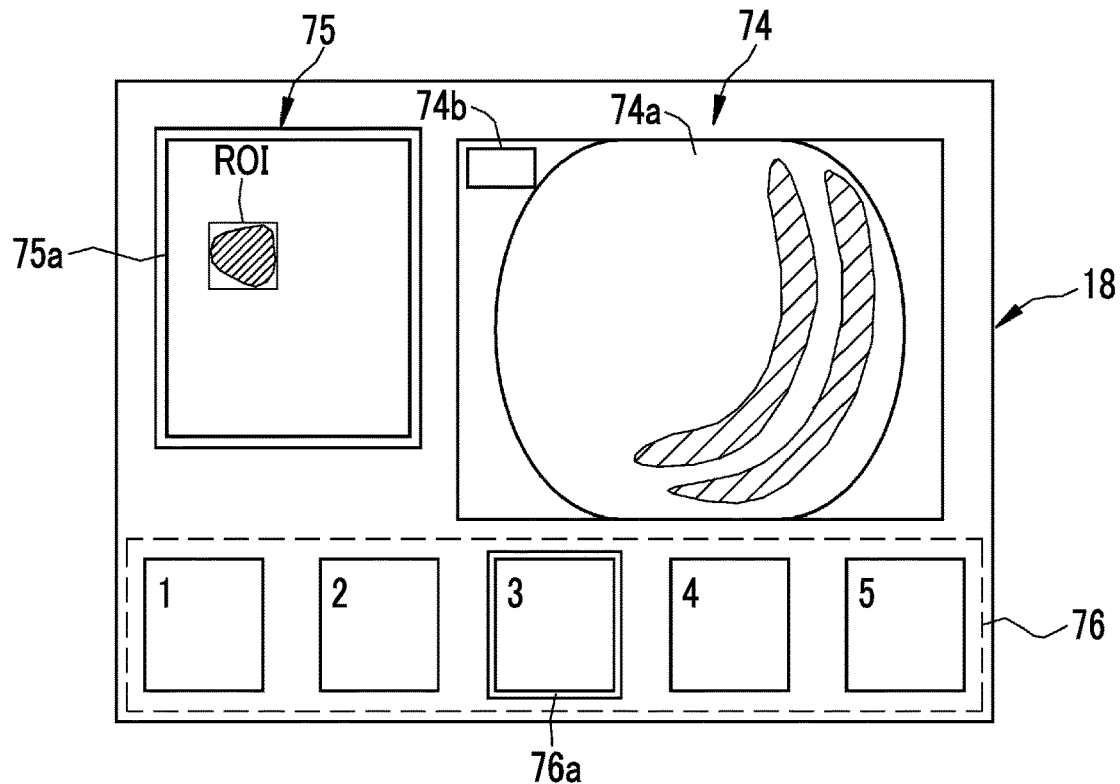
FIG. 6 is an image diagram of the monitor in a case where a target of interest disappears from the main screen.
Figure 7:
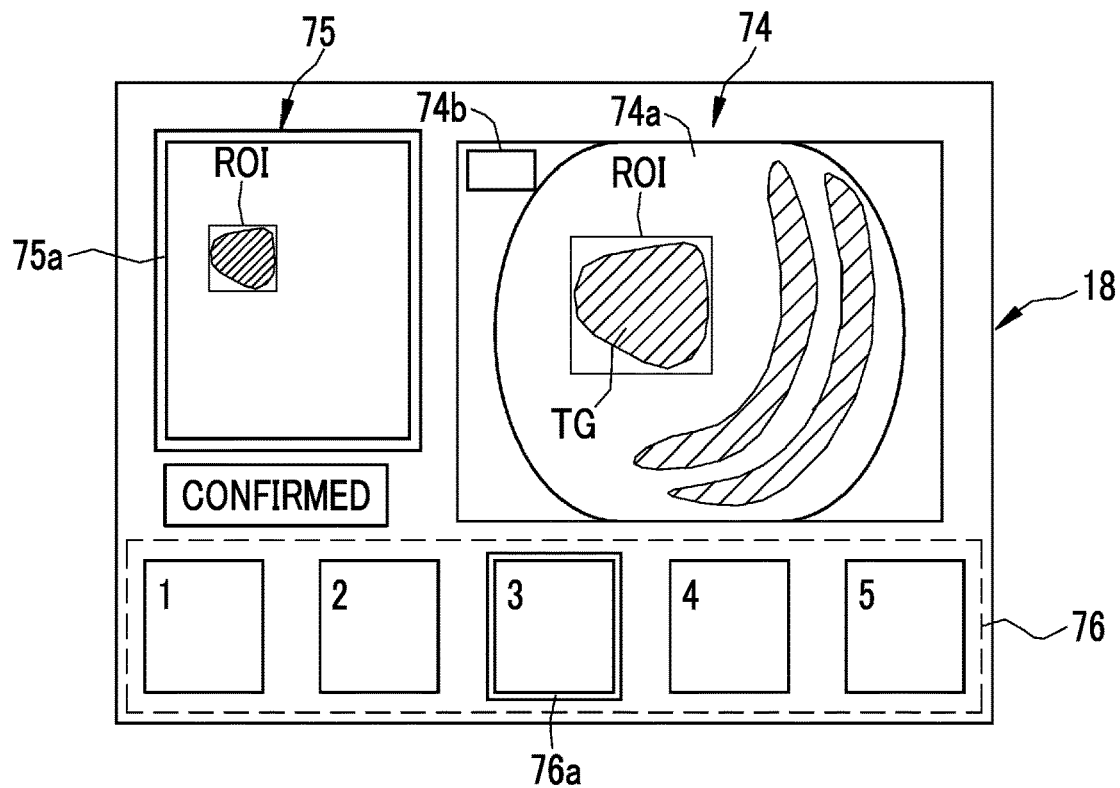
FIG. 7 is an image diagram of the monitor on which a message of "confirmed" is displayed.

As illustrated in FIG. 6, the display of the sub screen 75 is continuously performed for a certain period of time even after the target of interest TG is no longer displayed in the main screen 74. By performing continuously the display of the sub screen 75, it is possible for the user to notice that the target of interest TG is overlooked even in a case where the user has overlooked the target of interest TG such as a case where the moving speed of the endoscope 12 is high and the target of interest TG is passed instantly so that the target of interest TG disappears from the main screen 74 instantly or the like. After the target of interest TG is no longer displayed in the main screen 74, in order to notify the overlooking of the target of interest TG the frame 75a of the sub screen 75 may be displayed blinking or may be displayed in a different color from the first color.

At the time of the detection of the region of interest ROI, in order to record that the user has confirmed the target of interest TG it is preferable to perform a confirmation operation. As the confirmation operation, for example, after the main screen 74 is displayed, the user operates the endoscope 12 to cause the target of interest TG to be in the vicinity of the center of the main screen 74. In a case where the target of interest TG is maintained in the vicinity of the center and a certain period of time elapses, the confirmation signal generation unit 77 generates a region-of-interest confirmation signal. In a case where the region-of-interest confirmation signal is generated, a message of "confirmed" indicating that the user has confirmed the target of interest TG is displayed on the monitor 18. According to this, the color of the frame 75a of the sub screen 75 is changed to a second color (for example, "yellow color") different from the first color as an alert (second alert) indicating that the user has confirmed the target of interest TG.

In a case where the region-of-interest confirmation signal is generated, the color of the frame 76a of the screen of the static image in the static image list screen is also changed to the same second color as the color of the frame of the sub screen 75. At the time at which the target of interest TG cannot be displayed in the vicinity of the center, the region-of-interest confirmation signal may be generated in response to the operation of the user interface 19. Further, at the timing at which the region of interest is confirmed, the "confirmation of the region of interest" may be notified by displaying an icon such as an arrow on the monitor 18 in addition to a sound, vibration (vibrating the operation part 12b of the endoscope), and change of illumination light (change from white light to blue monochromatic light, or the like).

Figure 8:
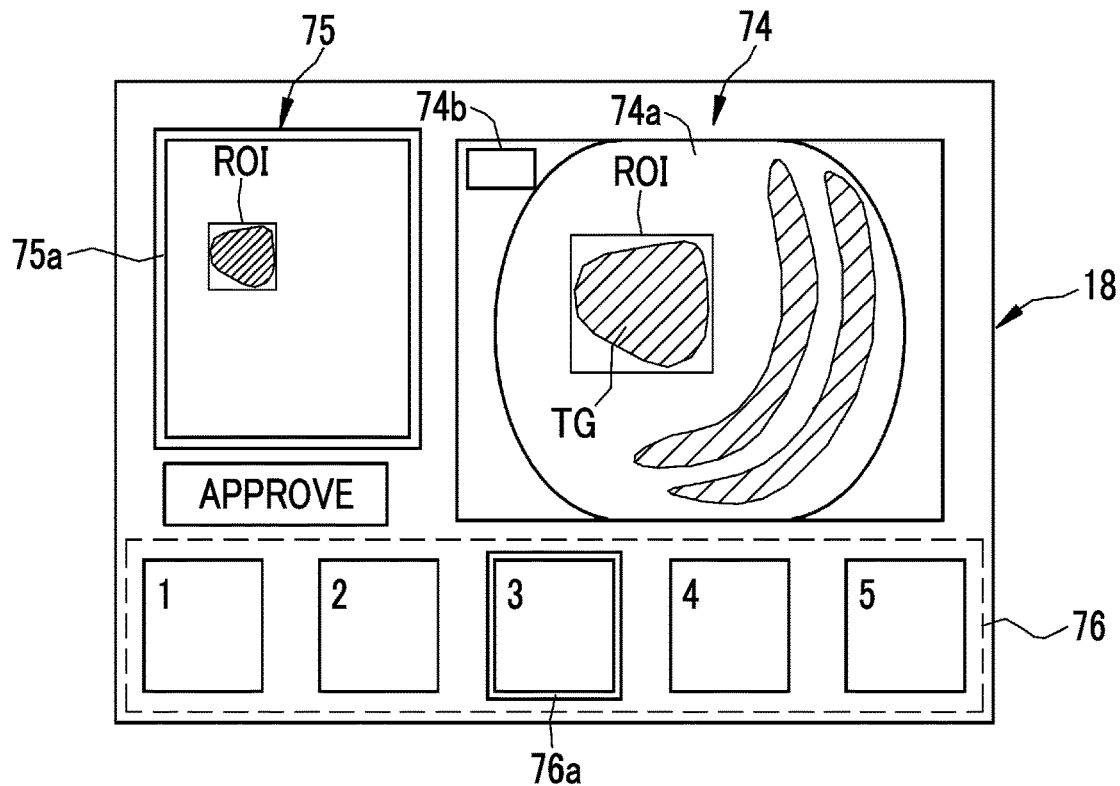
FIG. 8 is an image diagram of the monitor on which a message of "approve" is displayed.

After the confirmation of the target of interest TG, it is preferable to perform propriety determination on whether the region of interest ROI is correctly detected. For example, in a case where the user considers that the region of interest detected by the region-of-interest detection unit 70 is correctly detected, the user presses a region approval button 13c (refer to FIG. 2) provided to the operation part 12b once. Accordingly, the region determination instruction generation unit 78 issues an instruction indicating that the region of interest is correctly detected as a region determination instruction relating to the propriety of the detection of the region of interest. In this case, as illustrated in FIG. 8, a message of "approve" indicating that the region of interest is correctly detected is displayed. According to this, the color of the frame 75a of the sub screen 75 is changed to a third color (for example, "green color") different from the first and second colors as an alert (third alert) indicating that the region of interest is correctly detected.

The color of the frame 76a of the screen of the static image in the static image list screen is also changed to the same third color as the color of the frame of the sub screen. Further, in a case where it is determined that the region of interest is correctly detected, the fact that "the region of interest is correctly detected" may be notified by displaying an icon such as an arrow on the monitor 18 in addition to a sound, vibration (vibrating the operation part 12b of the endoscope), and change of illumination light (change from white light to blue monochromatic light, or the like).

Figure 9:
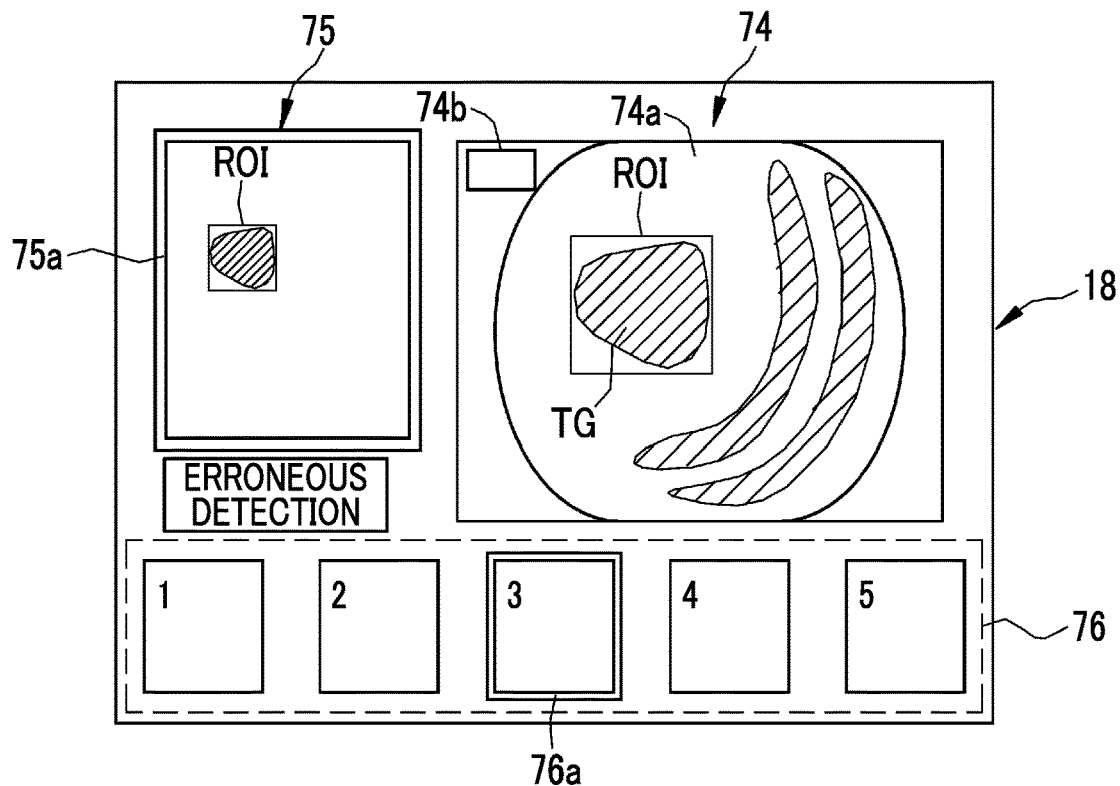
FIG. 9 is an image diagram of the monitor on which a message of "erroneous detection" is displayed.

In contrast, in a case where the user considers that the region of interest detected by the region-of-interest detection unit 70 is erroneously detected, the user presses the region approval button 13c (refer to FIG. 2) provided to the operation part 12b twice. Accordingly, the region determination instruction generation unit 78 issues an instruction indicating that the region of interest is erroneously detected as the region determination instruction relating to the propriety of the detection of the region of interest. In this case, as illustrated in FIG. 9, a message of "erroneous detection" indicating that the region of interest is erroneously detected is displayed. According to this, the color of the frame 75a of the sub screen 75 is changed to the third color (for example, "gray color") different from the first and second colors as an alert (fourth alert) indicating that the region of interest is erroneously detected.

The color of the frame 76a of the screen of the static image in the static image list screen is also changed to the same third color as the color of the frame of the sub screen. Further, in a case where it is determined that the region of interest is erroneously detected, the fact that "the region of interest is erroneously detected" may be notified by displaying an icon such as an arrow on the monitor 18 in addition to a sound, vibration (vibrating the operation part 12b of the endoscope), and change of illumination light (change from white light to blue monochromatic light, or the like).

The determination result of whether the region of interest is correctly detected is associated with the medical image obtained at the time of detection of the region of interest and is preserved in a memory (not illustrated) in the processor device 16, as learning data for the learning of the region-of-interest detection unit 70. In a case where the learning processing is selected, the region-of-interest detection unit 70 performs the learning processing by reading the learning data from the memory. By performing the learning processing, it is possible to improve the detection accuracy of the region of interest by the region-of-interest detection unit 70.

The overlooking determination unit 80 sequentially receives the medical image and the detection result of the region of interest from the region-of-interest detection unit 70, and calculates information for determining the overlooking of the target of interest used in the overlooking determination of the target of interest TG, from the medical image and the detection result of the region of interest. The overlooking determination unit 80 calculates an overlooking determination index value on the basis of the information for determining the overlooking of the target of interest. The overlooking determination index value is obtained by respectively multiplying weighting coefficients K1 to K4 and conversion coefficients C1 to C4 to four pieces of information of, for example, a movement direction D1 of the endoscope 12, a display time D2 of the target of interest TG in the main screen 74, a size D3 of the target of interest TG and a position D4 of the target of interest in the main screen 74 among the information for determining the overlooking of the target of interest, and adding the results (overlooking determination index value=k1×C1×D1+k2×C2×D2+k3×C3×D3+k4×C4×D4).

The conversion coefficients C1 to C4 are coefficients for converting the movement direction D1 of the endoscope 12, the display time D2 of the target of interest TG in the main screen 74, the size D3 of the target of interest TG, or the position D4 of the target of interest in the main screen 74 into numerical values for the overlooking determination index value. The conversion coefficients C1 to C4 are set to predetermined values.

Here, the movement direction of the endoscope 12 includes an insertion direction in which the endoscope 12 is inserted along the lumen, and in contrast, an extraction direction in which the endoscope 12 is extracted along the lumen. Whether the movement direction of the endoscope is the insertion direction or the extraction direction is determined from the information of the size and position of the target of interest TG In a case where the size of the target of interest TG is increased over time and the target of interest TG disappears from the lower end portion of the main screen 74, the movement direction of the endoscope 12 is determined to be the insertion direction. On the other hand, in a case where the size of the target of interest TG is decreased over time and the target of interest TG disappears from the vicinity of the center of the main screen 74, the movement direction of the endoscope 12 is determined to be the extraction direction.

In a case where the overlooking determination index value is calculated, for the movement direction D1 of the endoscope, the weighting coefficient K1 in case of the extraction direction is set to be greater than the weighting coefficient K1 in case of the insertion direction. This is for observing the observation target in more detail in case of the extraction direction than in case of the insertion direction. Further, for the display time D2 of the target of interest TG in the main screen 74, in a case where the display time until the region of interest disappears from the main screen 74 after being detected is shorter than a specific display time and a time from the target of interest TG disappears exceeds a specific disappearance time, the weighting coefficient K2 is set to be increased. In such a case, the moving speed of the endoscope 12 is high, the target of interest TG may be passed instantly, and thus there is a possibility of overlooking of the target of interest TG.

As the size D3 of the target of interest TG is smaller, the weighting coefficient K3 is set to be increased. This is because it is easy to overlook the target of interest TG as the target of interest TG is small. Further, as the position D4 of the target of interest in the main screen 74 is closer to the end portion of the main screen 74, the weighting coefficient K4 is set to be increased. In a case where the target of interest is at the end portion of the main screen 74, the target of interest instantly disappears from the main screen 74, and thus it is easy to overlook the target of interest.

In a case where the overlooking determination index value is determined to be greater than a predetermined overlooking determination threshold value, the overlooking determination unit 80 determines that the possibility that the target of interest TG is overlooked is high. In this case, the overlooking notification control unit 82 performs a control relating to an overlooking occurrence notification indicating that the possibility that the target of interest TG is overlooked is high. The display control unit 66 causes the monitor 18 to display the overlooking occurrence notification according to the control of the overlooking notification control unit 82. By the overlooking occurrence notification being displayed on the monitor 18, it is possible for the user to notice the overlooking of the target of interest TG In addition to the overlooking occurrence notification, by continuously displaying the sub screen 75 for a certain period of time even after the target of interest TG disappears from the main screen 74, it is possible to prevent the overlooking twice over.

Figure 10:
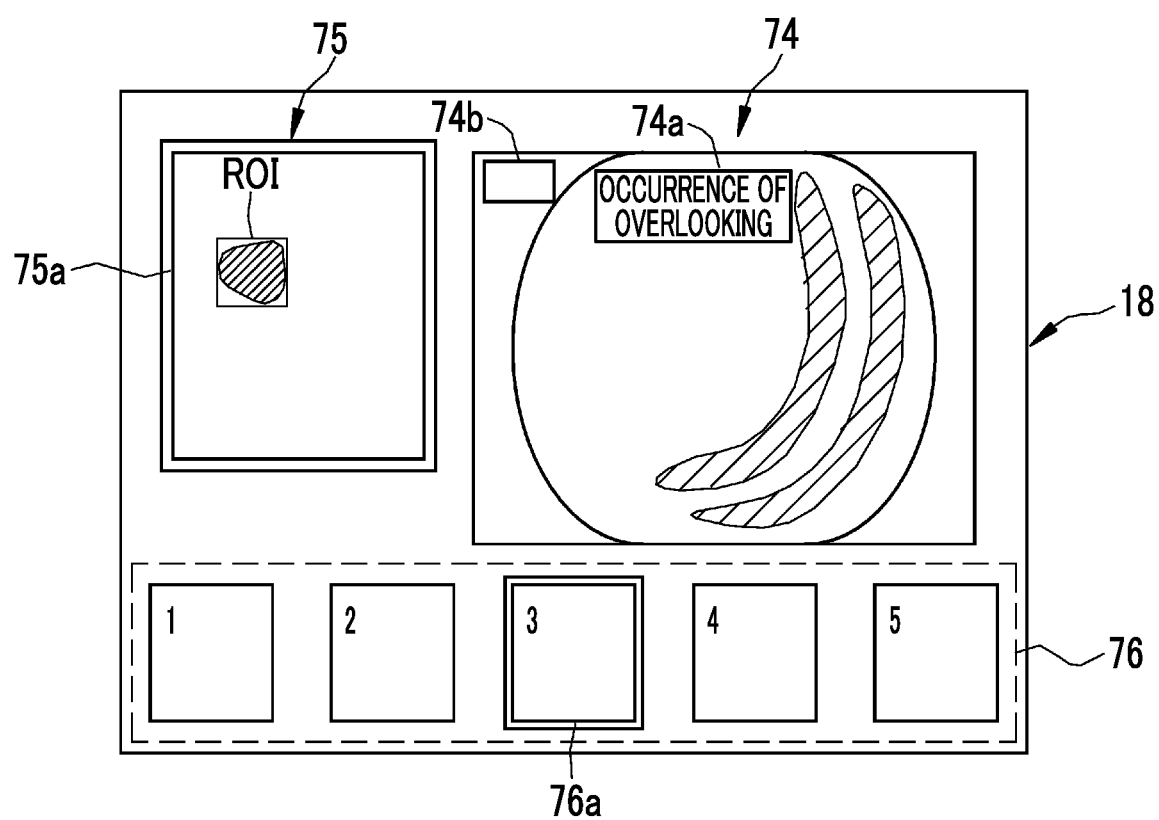
FIG. 10 is an image diagram of the monitor on which a message of "occurrence of overlooking" is displayed.

As illustrated in FIG. 10, as the overlooking occurrence notification, for example, a message of "occurrence of overlooking" is displayed on the monitor 18. Further, the "occurrence of overlooking" may be notified by displaying an icon such as an arrow on the monitor 18 in addition to a sound, vibration (vibrating the operation part 12*b* of the endoscope), and change of illumination light (change from white light to blue monochromatic light, or the like). Further, the notification may be performed by different sounds depending on the disappearance directions of the target of interest. For example, in a case where the target of interest disappears from the lower end portion of the sub screen 75, the notification is performed by a first sound, and in a case where the target of interest disappears from the center portion of the sub screen 75, the notification is performed by a second sound different from the first sound.

In contrast, in a case where the overlooking determination index value is determined to be equal to or less than the predetermined overlooking determination threshold value, the overlooking determination unit 80 determines that the possibility that the target of interest TG is overlooked is low. In this case, the overlooking occurrence notification is not performed. In this manner, the overlooking occurrence notification is not performed unnecessarily, and thus it is possible for the user to avoid a troublesome state. It is preferable that the determination result of whether the target of interest TG is overlooked by the overlooking determination unit 80 is preserved in the memory (not illustrated) in the processor device 16.

Figure 11:
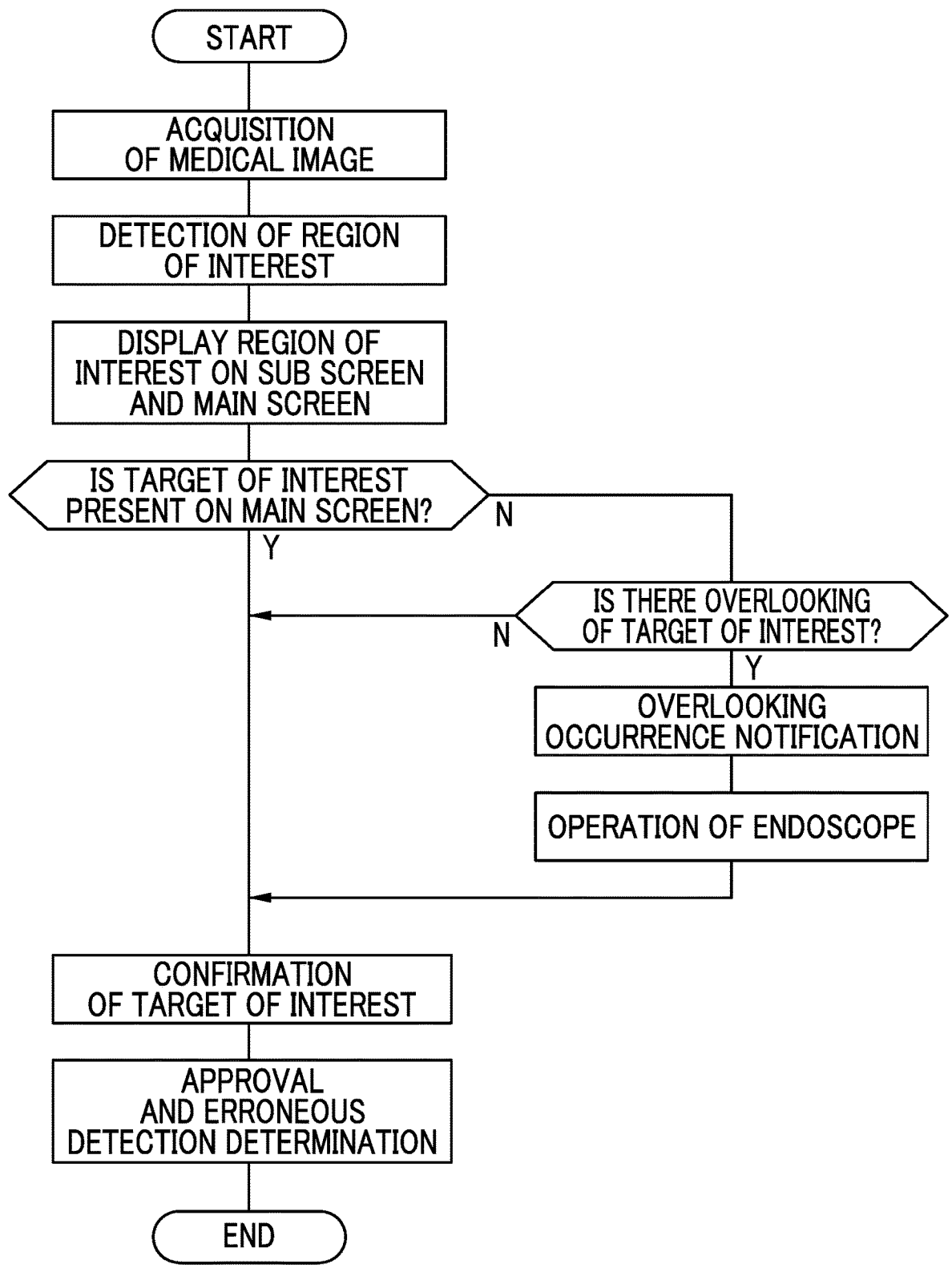
FIG. 11 is a flowchart illustrating a series of flow of preventing overlooking of the target of interest.

Next, a series of flow of preventing overlooking of the target of interest is described with reference to the flowchart of FIG. 11. The observation target is imaged to obtain the medical image. The video of the medical image is displayed on the main screen 74 of the monitor 18. In addition, the region-of-interest detection unit 70 detects the region of interest from the medical image. In a case where the target of interest TG appears on the main screen 74 and the region of interest is detected by the region-of-interest detection unit 70, the display of the sub screen 75 on the monitor 18 is started. In the sub screen 75, the static image of the medical image including the region of interest ROI and the target of interest TG included in the region of interest ROI is displayed. According to this, the region of interest ROI is displayed with respect to the target of interest TG also on the main screen 74.

In a case where the user notices the target of interest TG on the main screen 74, the user performs the confirmation operation of the target of interest TG and determines the propriety relating to the detection of the region of interest. In contrast, even in a case where the user overlooks the target of interest TG on the main screen 74 and the target of interest TG is no longer displayed on the main screen 74, the sub screen 75 is continuously displayed for a certain period of time. In this manner, it is possible for the user to notice the overlooking of the target of interest TG.

The overlooking determination unit 80 calculates the overlooking determination index value, and determines whether the calculated overlooking determination index value exceeds the overlooking determination threshold value. In a case where the overlooking determination index value exceeds the overlooking determination threshold value, the overlooking occurrence notification is performed. In a case where the overlooking occurrence notification is performed, the endoscope 12 is operated to return to the position where the target of interest TG is present, so that the target of interest TG is displayed on the main screen 74 again. In a case where the target of interest TG is displayed on the main screen 74, the confirmation operation of the target of interest TG and the determination of the propriety relating to the detection of the region of interest are performed.

Figure 12:
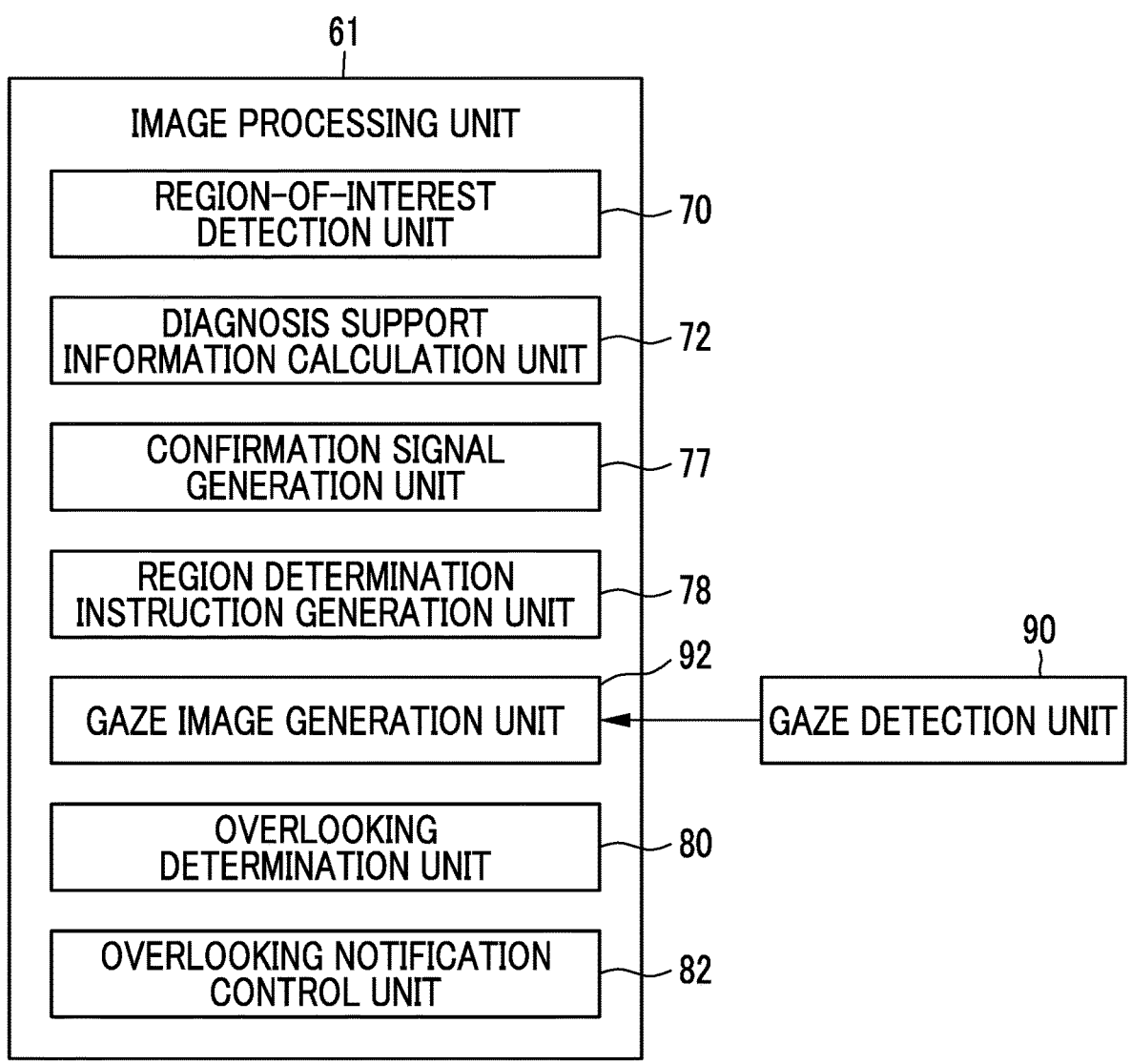
FIG. 12 is a block diagram illustrating a function of an image processing unit comprising a gaze image generation unit.

In the first embodiment, the overlooking determination unit 80 determines the overlooking of the target of interest TG on the basis of the medical image or the detection result of the region of interest from the region-of-interest detection unit 70, but instead of this, as illustrated in FIG. 12, a gaze detection unit 90 may detect the user's gaze directed at the region of interest and determine the overlooking of the target of interest TG on the basis of the detection result of the gaze.

Figure 13:
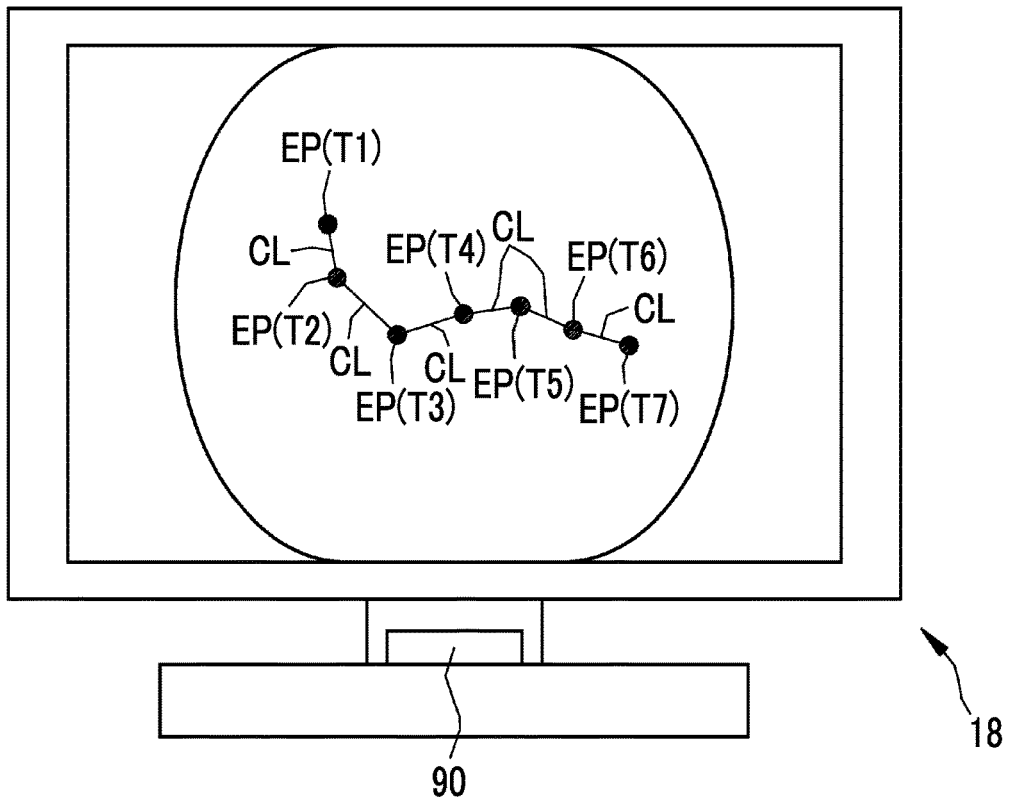
FIG. 13 is an image diagram of a gaze image in which a gaze point EP is displayed.

As illustrated in FIG. 13, the gaze detection unit 90 is provided on the front surface of the monitor 18, and detects a gaze point indicating the user's gaze directed at the monitor 18. A gaze image generation unit 92 generates a gaze image on the basis of information relating to the gaze point detected by the gaze detection unit 90. In the gaze image, a plurality of gaze points EP(T1) to EP(TN) acquired at certain time intervals T1 to TN (N=7 in FIG. 13, the larger number of N means new in time) are displayed and the gaze points EP(T1) to EP(TN) are connected by connection lines CL so that the trajectory of the gaze can be understood. The gaze point after a certain time interval is deleted from the gaze image, and instead, the latest gaze point is displayed.

Figure 14:
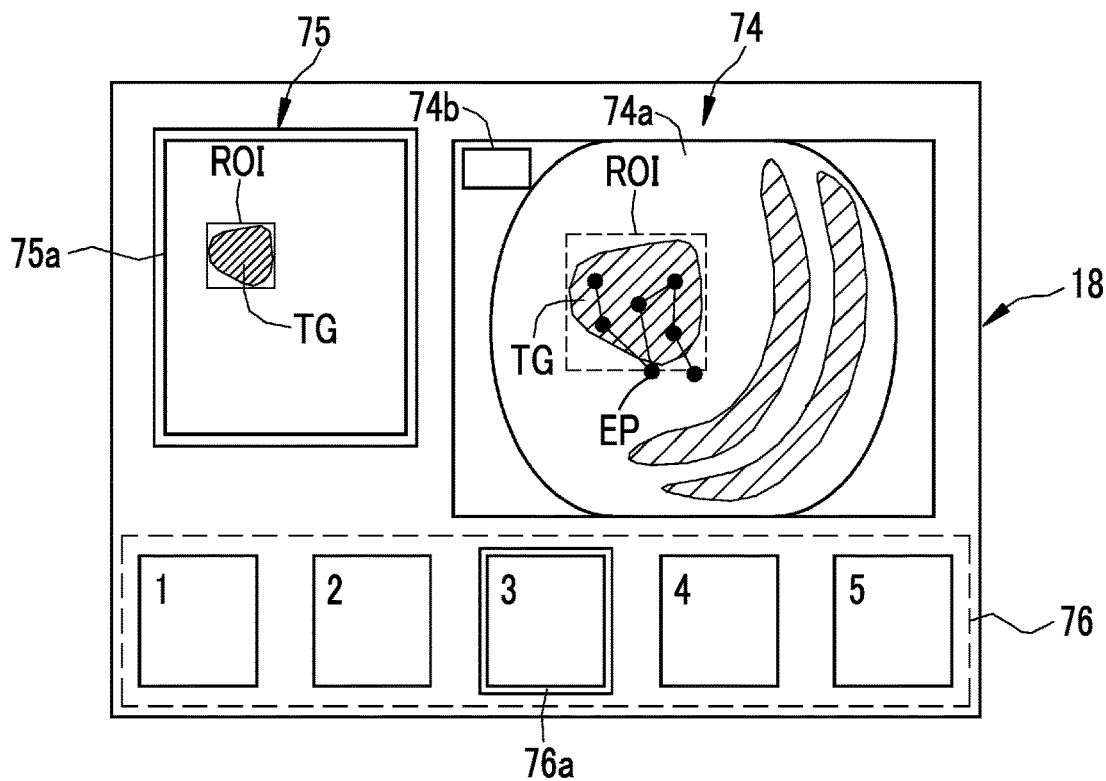
FIG. 14 is an image diagram of a composite image obtained by composing a medical image in which a region of interest ROI is displayed and a gaze image.

In a case where the gaze image is generated, as illustrated in FIG. 14, a composite image obtained by composing the medical image in which the region of interest ROI is displayed and the gaze image is displayed on the monitor 18. With the composite image, the positional relationship between the region of interest ROI and the gaze point EP that the user is currently gazing at can be understood. Further, the time during which the gaze point EP is included in the region of interest ROI can be understood.

The overlooking determination unit 80 counts the time during which the gaze point EP is included in the region of interest ROI, as the observation time. In a case where the observation time is shorter than a specific observation time, the overlooking determination unit 80 determines that the possibility that the target of interest TG is overlooked is high. The overlooking occurrence notification as described above is performed. In contrast, in a case where the observation time is longer than the specific observation time, the overlooking determination unit 80 determines that the possibility that the target of interest TG is overlooked is low. In this case, the overlooking occurrence notification is not performed.

Second Embodiment

Figure 15:
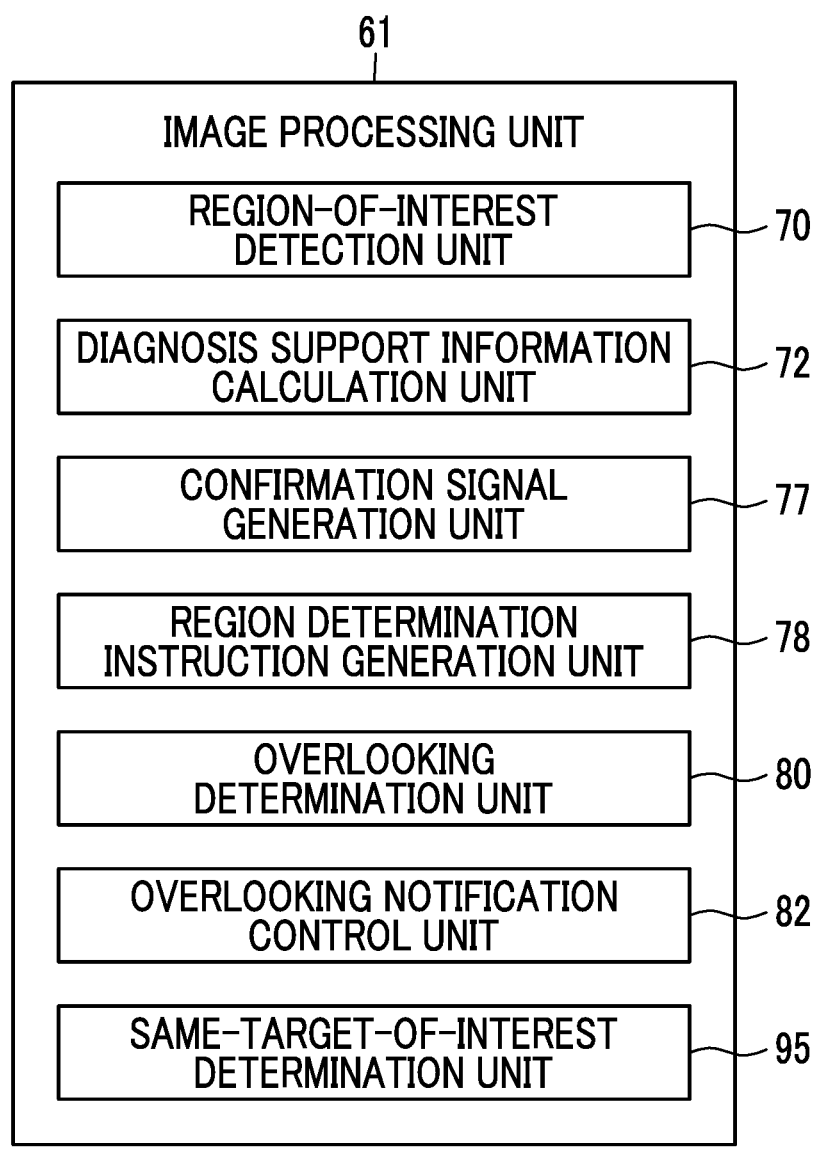
FIG. 15 is a block diagram illustrating a function of an image processing unit of a second embodiment.

In a second embodiment, processing of preventing the same target of interest from being notified a plurality of times as the region of interest is performed. Specifically, determination on whether a first target of interest displayed in the main screen 74 at a first timing and a second target of interest displayed in the main screen 74 at a second timing which is different from the first timing are the same is performed. The determination on whether the targets of interest are the same is performed in a same-target-of-interest determination unit 95 illustrated in FIG. 15. The display control unit 66 performs a control of displaying or not displaying the second target of interest as the region of interest ROI on the main screen 74 or the sub screen 75 on the basis of the determination result of the same-target-of-interest determination unit 95. In a case where it is determined that the first target of interest and the second target of interest are the same, when the ID number of the first target of interest and the ID number of the second target of interest are different, processing of integrating the ID numbers into one of the ID numbers is performed.

Figure 16:
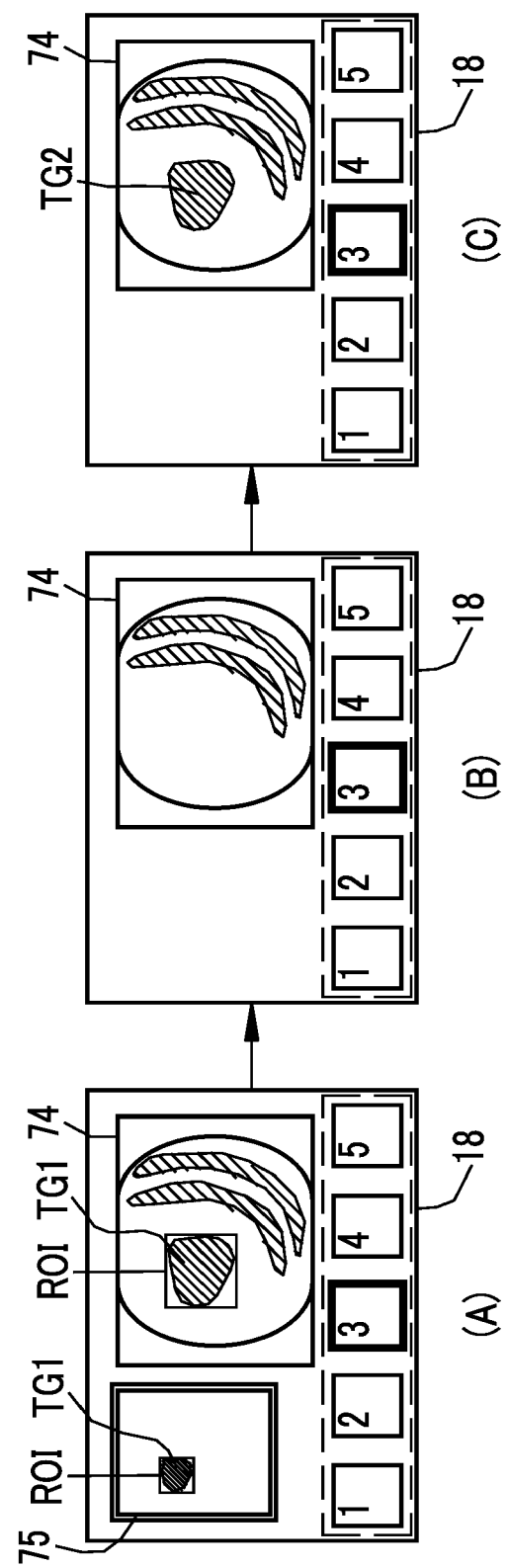
FIG. 16 is an explanatory diagram illustrating that in a case where a first target of interest TG1 and a second target of interest TG2 are the same, the second target of interest is not displayed as the region of interest.

For example, after the first target of interest TG1 is displayed on the main screen 74 at the first timing as illustrated in FIG. 16(A), in a case where the first target of interest TG1 is no longer displayed on the main screen 74 by being hidden by folds and the like due to pulsation or the like as illustrated in FIG. 16(B), the display of the region of interest ROI on the main screen 74 and the sub screen 75 is not performed. As illustrated in FIG. 16(C), in a case where the folds and the like disappear from the main screen 74 and the second target of interest TG2 is displayed on the main screen 74 at the second timing, the same-target-of-interest determination unit 95 determines whether the first target of interest TG1 and the second target of interest TG2 are the same. In this case, since the target of interest has been hidden by the folds and the like, it is determined that the first target of interest TG1 and the second target of interest TG2 are the same. In this case, the second target of interest is not displayed as the region of interest ROI in the main screen 74 and the sub screen 75 by the display control unit 66. In this manner, a duplicate notification on the same target of interest is avoided.

In a case where it is determined that the first target of interest TG1 and the second target of interest TG2 are the same, it is preferable that the display of an icon such as an arrow on the monitor 18 in addition to a sound, vibration (vibrating the operation part 12b of the endoscope), and change of illumination light (change from white light to blue monochromatic light, or the like) is not performed in addition to not displaying the region of interest ROI. Further, in a case where it is determined that the first target of interest TG1 and the second target of interest TG2 are the same, it is preferable that the static image in the sub screen 75 is not updated.

However, in a case where the first target of interest is detected in an outward path in which the distal end part 12d of the endoscope 12 is mainly moved in the insertion direction and contrary, the second target of interest same as the first target of interest is detected in a return path in which the distal end part 12d of the endoscope 12 is mainly moved in the extraction direction, it is preferable that the second target of interest is displayed as the region of interest ROI even in a case where the same-target-of-interest determination unit 95 determines that the first target of interest and the second target of interest are the same. In this case, in order to determine the outward path or the return path, it is necessary to detect whether the movement direction of the endoscope 12 is the insertion direction or the extraction direction from the image features as described in the first embodiment. The outward path or the return path may be determined depending on whether the time interval from the detection of the first target of interest to the detection of the second target of interest is within a specific time interval.

Figure 17:
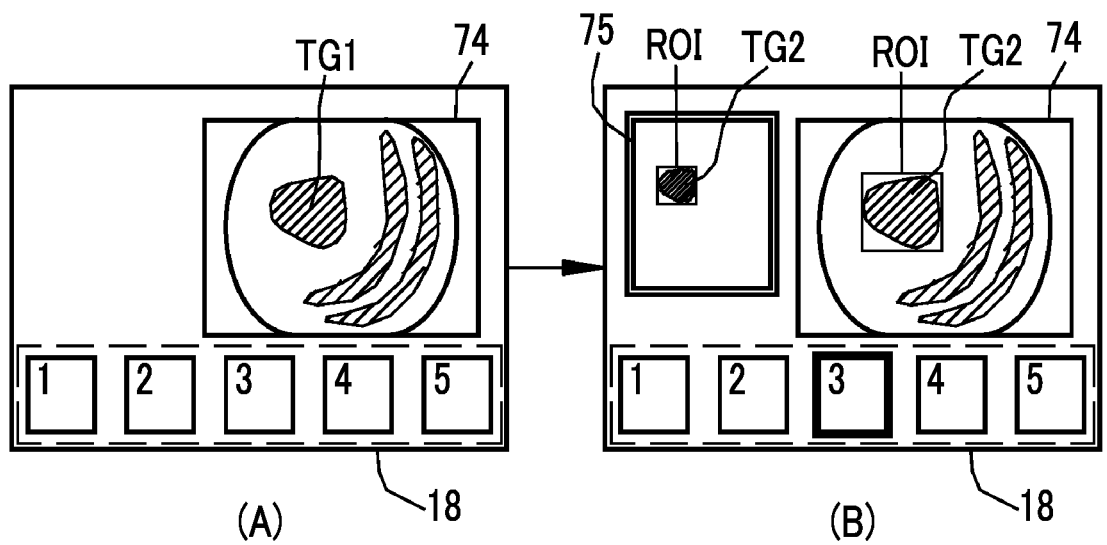
FIG. 17 is an explanatory diagram illustrating that in a case where the first target of interest TG1 and the second target of interest TG2 are the same, the first target of interest is not displayed as the region of interest and the second target of interest is displayed as the target of interest.

For example, as illustrated in FIG. 17(A), at the timing (first timing) at which the first target of interest is detected in the outward path, since the first target of interest TG1 is moved in the insertion direction, the region of interest ROI is not displayed. In contrast, as illustrated in FIG. 17(B), at the timing (second timing) at which the second target of interest TG2 is detected in the return path, even in a case where the second target of interest TG2 is the same as the first target of interest, since the second target of interest TG2 is moved in the extraction direction, the display control unit 66 causes the second target of interest TG2 to be displayed as the region of interest ROI. In this manner, it is possible to remind the user whether he/she has not overlooked the target of interest.

In the processing of determining whether the targets of interest are the same by the same-target-of-interest determination unit 95, in a case where the first target of interest and the second target of interest are displayed on the main screen 74 at different timings, it is preferable to perform motion flow tracking, for example. In addition, in a case where the first target of interest disappears from the main screen 74, it is preferable to perform the determination processing by matching the second target of interest to the static image of the first target of interest or the image around of the first target of interest. Further, the determination on whether the targets of interest are the same may be performed by the similarity between the discrimination score of the first target of interest and the discrimination score of the second target of interest. The determination on whether the targets of interest are the same may be performed by comparing an insertion length of the insertion part 12a of the endoscope at the time of the detection of the first target of interest with the insertion length of the insertion part 12a of the endoscope at the time of the detection of the second target of interest. Further, the determination on whether the targets of interest are the same may be performed by comparing the detection time indicating the time at which the first target of interest is detected with the detection time indicating the time at which the second target of interest is detected. The fact that the first target of interest and the second target of interest are the same includes a case where the image similarity is high even though the first target of interest and the second target of interest are not completely the same, in addition to a case where the first target of interest and the second target of interest are completely the same.

In the embodiment, examples of the blood vessel index value calculated in the diagnosis support information calculation unit 72 include a blood vessel density, a blood vessel thickness, the number of blood vessels, the number of branches, a branch angle, a distance between branch points, the number of intersections, a change in thickness, an interval, a depth based on mucous membrane, a height difference, a tilt, contrast, a color, a change in color, a meandering degree, a blood concentration, oxygen saturation, a ratio of arteries, a ratio of veins, a concentration of an administered pigment, a traveling pattern, and a blood flow.

The blood vessel density is represented by the ratio of the blood vessels included in a specific region occupying the image. The blood vessel thickness (blood vessel diameter) is a distance between the boundary lines of the blood vessel and the mucous membrane, and for example, is counted by counting the number of pixels along a short direction of the blood vessel from the edge of the detected blood vessel through the blood vessel. Accordingly, the blood vessel thickness is the number of pixels, but in a case where the imaging distance, the zoom magnification, or the like at the time of capturing the medical image is known, the blood vessel thickness can be converted into a length unit such as "µm" as necessary.

The number of blood vessels is the number of blood vessels detected in the entire medical image or in the region of interest. The number of blood vessels is calculated using the number of branch points (number of branches) of the detected blood vessel, the number of intersections (number of intersections) with other blood vessels, or the like. The branch angle of the blood vessel is an angle formed by two blood vessel at the branch point. The distance between the branch points is a straight line distance between any branch point and its next branch point or a length along the blood vessel from any branch point to its next branch point.

The number of intersections of the blood vessels is the number of intersections at which blood vessels having different depth from the mucous membrane intersect on the medical image. More specifically, the number of intersections of the blood vessels is the number of blood vessels, which are at a relatively shallow position from the mucous membrane, crossing the blood vessels which are at a relatively deep position.

The change in thickness of the blood vessel is blood vessel information relating to the variation in thickness of the blood vessel, and is caliber variation. The change in thickness of the blood vessel is a change rate (also referred to as a dilation degree) of the blood vessel diameter. The change rate of the blood vessel diameter is obtained by "change rate of blood vessel diameter (%)=minimum diameter/maximum diameter×100" by using the thickness of the thinnest portion (minimum diameter) of the blood vessel and the thickness of the thickest portion (maximum diameter) of the blood vessel.

In a case where a medical image obtained by imaging an observation target in a past inspection, and a medical image obtained by imaging the same observation target in a subsequent new inspection are used, a temporal change from the thickness of the blood vessel detected from the medical image obtained in the past inspection to the thickness of the same blood vessel detected from the medical image obtained in the subsequent new inspection may be adopted as the change in thickness of the blood vessel.

As the change in thickness of the blood vessel, a percentage of a small diameter portion or a percentage of a large diameter portion may be calculated. The small diameter portion is a portion having a thickness equal to or less than a threshold value, and the large diameter portion is a portion having a thickness greater than the threshold value. The percentage of the small diameter portion is obtained by "percentage of the small diameter portion (%)=length of small diameter portion/length of blood vessel×100". Similarly, the percentage of the large diameter portion is obtained by "percentage of large diameter portion (%)=length of large diameter portion/length of blood vessel×100".

The complexity of the change in thickness of the blood vessel (hereinafter, referred to as "complexity of thickness change") is blood vessel information representing how complicated the change is in a case where the thickness of the blood vessel is changed, and is blood vessel information calculated by combining a plurality of pieces of blood vessel information (that is, change rate of a blood vessel diameter, percentage of a small diameter portion, or percentage of a large diameter portion) representing the change in thickness of the blood vessel. The complexity of thickness change can be obtained by, for example, the product of the change rate of the blood vessel diameter and the percentage of the small diameter portion.

The length of the blood vessel is the number of pixels counted along the longitudinal direction of the detected blood vessel.

The interval of the blood vessel is the number of pixels representing the mucous membrane between edges of the detected blood vessel. In a case where the number of detected blood vessels is one, there is no value for the interval of the blood vessel.

The depth of the blood vessel is measured based on the mucous membrane (more specifically, the surface of the mucous membrane). The depth of the blood vessel based on the mucous membrane can be calculated on the basis of the color of the blood vessel, for example. In case of a special observation image, since the blood vessel positioned near the surface of the mucous membrane is represented by a color of magenta and the blood vessel positioned far from the surface of the mucous membrane and deep from the mucous membrane is represented by a color of cyan, the depth of the blood vessel based on the mucous membrane is calculated for each pixel on the basis of the balance of the signals of R, and B colors of the pixel detected as the blood vessel.

The height difference of the blood vessel is the magnitude of the difference in depth of the blood vessel. For example, the height difference of one blood vessel of interest is obtained by a difference between the depth of the deepest portion (maximum depth) of the blood vessel and a depth of the shallowest portion (minimum depth). In a case where the depth is constant, the height difference is zero.

The tilt of the blood vessel is the change rate of the depth of the blood vessel, and is calculated using the length of the blood vessel and the depth of the blood vessel. That is, the tilt of the blood vessel is obtained by "tilt of blood vessel=depth of blood vessel/length of blood vessel". The blood vessel may be divided into a plurality of sections, and the tilt of the blood vessel may be calculated in each section.

The area of the blood vessel is the number of pixels detected as the blood vessel or a value proportional to the number of pixels detected as the blood vessel. The area of the blood vessel is calculated for the inside of the region of interest, the outside of the region of interest, or the entire medical image.

The contrast of the blood vessel is a contrast relative to the mucous membrane of the observation target. The contrast of the blood vessel is calculated by, for example, "$Y_V/Y_M$" or "$(Y_V-Y_M)/(Y_V+Y_M)$" using the luminance $Y_V$ of the blood vessel and the luminance $Y_M$ of the mucous membrane.

The color of the blood vessel is RGB values of the pixels representing the blood vessel. The change in color of the blood vessel is a difference or a ratio between the maximum value and the minimum value of each of the RGB values of the pixels representing the blood vessel. For example, a ratio of the maximum value and the minimum value of the pixel value of the B pixel, a ratio of the maximum value and the minimum value of the pixel value of the G pixel, or a ratio of the maximum value and the minimum value of the pixel value of the R pixel representing the blood vessel represents the change in color of the blood vessel. Of course, the colors may be converted into complementary colors, and the color of the blood vessel and the change in color of the blood vessel may be calculated for each value of cyan, magenta, yellow, green, and the like.

The meandering degree of the blood vessel is blood vessel information representing the breadth of a range in which the blood vessel travels meandering. The meandering degree of the blood vessel is the area (number of pixels) of the minimum rectangle including the blood vessel of which the meandering degree is to be calculated. Further, a ratio of the length of the blood vessel with respect to a straight line distance between a start point and an end point of the blood vessel may be adopted as the meandering degree of the blood vessel.

The blood concentration of the blood vessel is blood vessel information proportional to the amount of hemoglobin contained in blood vessel. Since a ratio (G/R) of the pixel value of the G pixel to the pixel value of the R pixel representing the blood vessel is proportional to the amount of hemoglobin, it is possible to calculate the blood concentration for each pixel by calculating the value of G/R.

The oxygen saturation of the blood vessel is the amount of oxyhemoglobin relative to the total amount of hemoglobin (total amount of oxyhemoglobin and reduced hemoglobin). The oxygen saturation can be calculated using the medical image obtained by imaging the observation target with light (for example, blue light having a wavelength of about 470±10 nm) in a specific wavelength range where the difference of the light absorption coefficient between oxyhemoglobin and reduced hemoglobin is large. In case of using blue light having a wavelength of about 470±10 nm, since the pixel value of the B pixel representing the blood vessel has a correlation with the oxygen saturation, it is possible to calculate the oxygen saturation of each pixel representing the blood vessel by using a table or the like in which the pixel value of the B pixel is associated with the oxygen saturation.

The ratio of arteries is a ratio of the number of pixels of the arteries to the number of pixels of all of the blood vessels. Similarly, the ratio of veins is a ratio of the number of pixels of the veins to the number of pixels of all of the blood vessels. The arteries and the veins can be distinguished by the oxygen saturation. For example, in a case where the blood vessel having oxygen saturation of 70% or greater is regarded as the artery and the blood vessel having oxygen saturation of less than 70% is regarded as the vein, since the detected blood vessel can be classified into arteries and veins, it is possible to calculate the ratio of arteries and the ratio of veins.

The concentration of the administered pigment is a concentration of a pigment sprayed on the observation target or a pigment injected into the blood vessel by intravenous injection. The pigment of the administered pigment is calculated by a ratio of the pixel value of the pigment color to the pixel value of the pixel other than the pigment color, for example. For example, in a case where a pigment that colors blue is administered, a ratio B/G of the B image and the G image, a ratio B/R of the B image and the R image, and the like represent the concentration of the pigment fixed (or temporarily attached) to the observation target.

The traveling pattern of the blood vessel is blood vessel information relating to a traveling direction of the blood vessel. The traveling pattern of the blood vessel is an average angle (traveling direction) of the blood vessels relative to a reference line set arbitrarily, a dispersion (variance of the traveling direction) of angles formed by the blood vessels relative to the reference line set in arbitrarily.

The blood flow (referred to as a blood flow velocity) of the blood vessel is the number of red blood cells passing through per unit time. In a case where the ultrasound probe is used in combination through the forceps channel of the endoscope 12 or the like, the blood flow of the blood vessel can be obtained by calculating the Doppler shift frequency of each pixel representing the blood vessel in the medical image using a signal obtained by the ultrasound probe.

In the embodiment, the invention is applied to the endoscope system that performs processing on the endoscopic image as one of the medical images. However, the invention can also be applied to a medical image processing system that processes medical images other than the endoscopic image. The invention can also be applied to a diagnosis support apparatus for performing diagnosis support for a user using the medical image. The invention can also be applied to a medical service support apparatus for supporting the medical service, such as a diagnostic report, using the medical image.

It is preferable that the medical image is a normal light image that is obtained from the application of light in a white-light wavelength range or light in a plurality of wavelength ranges as the light in a white-light wavelength range.

It is preferable that the medical image is a special light image that is obtained from the application of light in a specific wavelength range, and the specific wavelength range is a range narrower than the white-light wavelength range. It is preferable that the specific wavelength range is included in a blue-light wavelength range or a green-light wavelength range of a visible-light wavelength range. It is preferable that the specific wavelength range includes a wavelength range of 390 nm to 450 nm or 530 nm to 550 nm, and light in the specific wavelength range has a peak wavelength in a wavelength range of 390 nm to 450 nm or 530 nm to 550 nm.

It is preferable that the specific wavelength range is included in a red-light wavelength range of a visible-light wavelength range. It is preferable that the specific wavelength range includes a wavelength range of 585 nm to 615 nm or 610 nm to 730 nm, and light in the specific wavelength range has a peak wavelength in a wavelength range of 585 nm to 615 nm or 610 nm to 730 nm.

It is preferable that the specific wavelength range includes a wavelength range where a light absorption coefficient in oxyhemoglobin is different from that in reduced hemoglobin, and light in the specific wavelength range has a peak wavelength in a wavelength range where a light absorption coefficient in oxyhemoglobin is different from that in reduced hemoglobin. It is preferable that the specific wavelength range includes a wavelength range of 400±10 nm, 440±10 nm, 470±10 nm, or 600 nm to 750 nm, and light in the specific wavelength range has a peak wavelength in a wavelength range of 400±10 nm, 440±10 nm, 470±10 nm, or 600 nm to 750 nm.

It is preferable that the medical image is an in-vivo image of the inside of a living body, and the in-vivo image has information of fluorescence emitted by fluorescent materials in the living body. It is preferable that the fluorescence is obtained from the application of excitation light of which a peak wavelength is included in a wavelength range of 390 nm to 470 nm, to the inside of the living body.

It is preferable that the medical image is an in-vivo image of the inside of a living body, and the specific wavelength range is an infrared wavelength range. It is preferable that the specific wavelength range includes a wavelength range of 790 nm to 820 nm or 905 nm to 970 nm, and light in the specific wavelength range has a peak wavelength in a wavelength range of 790 nm to 820 nm or 905 nm to 970 nm.

It is preferable that an image acquisition unit includes a special light image acquisition unit that acquires a special light image having a signal in the specific wavelength range on the basis of a normal light image obtained from the application of light in a white-light wavelength range or light in a plurality of wavelength ranges as the light in a white-light wavelength range, and the medical image is the special light image.

It is preferable that the signal in the specific wavelength range is obtained from an arithmetic operation based on color information about RGB or CMY included in the normal light image.

It is preferable that a computed image generation unit generating a computed image from an arithmetic operation based on at least one of the normal light image that is obtained from the application of light in a white-light wavelength range or light in a plurality of wavelength ranges as the light in a white-light wavelength range or the special light image that is obtained from the application of light in a specific wavelength range is provided, and the medical image is the computed image.

Figure 18:
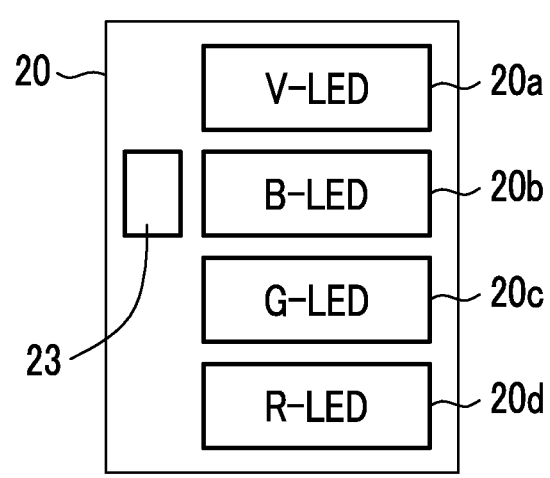
FIG. 18 is a block diagram illustrating a light source unit comprising a plurality of LEDs.

In the embodiment, it is preferable that illumination light is emitted by using LEDs of four colors, such as a violet light emitting diode (V-LED) 20a, a blue light emitting diode (B-LED) 20b, a green light emitting diode (G-LED) 20c, and a red light emitting diode (R-LED) 20d, and a wavelength cut filter 23 as the light source unit 20, as illustrated in FIG. 18.

The V-LED 20a emits violet light V in a wavelength range of 380 nm to 420 nm. The B-LED 20b emits blue light B in a wavelength range of 420 nm to 500 nm. Among the blue light B emitted from the B-LED 20b, at least light in a wavelength range on the longer wavelength side than a peak wavelength of 450 nm is cut by the wavelength cut filter 23. In this manner, blue light Bx transmitted through the wavelength cut filter 23 is within a wavelength range of 420 nm to 460 nm. The reason of cutting light in a wavelength range on the longer wavelength side than 460 nm is that light in a wavelength range on the longer wavelength side than 460 nm is a factor reducing a blood vessel contrast of the blood vessel as the observation target. The wavelength cut filter 23 may attenuate light in a wavelength range on the longer wavelength side than 460 nm instead of cutting light in a wavelength range on the longer wavelength side than 460 nm. The G-LED 20c emits green light G having a wavelength range of 480 nm to 600 nm. The R-LED 20d emits red light R having a wavelength range of 600 nm to 650 nm.

Figure 19:
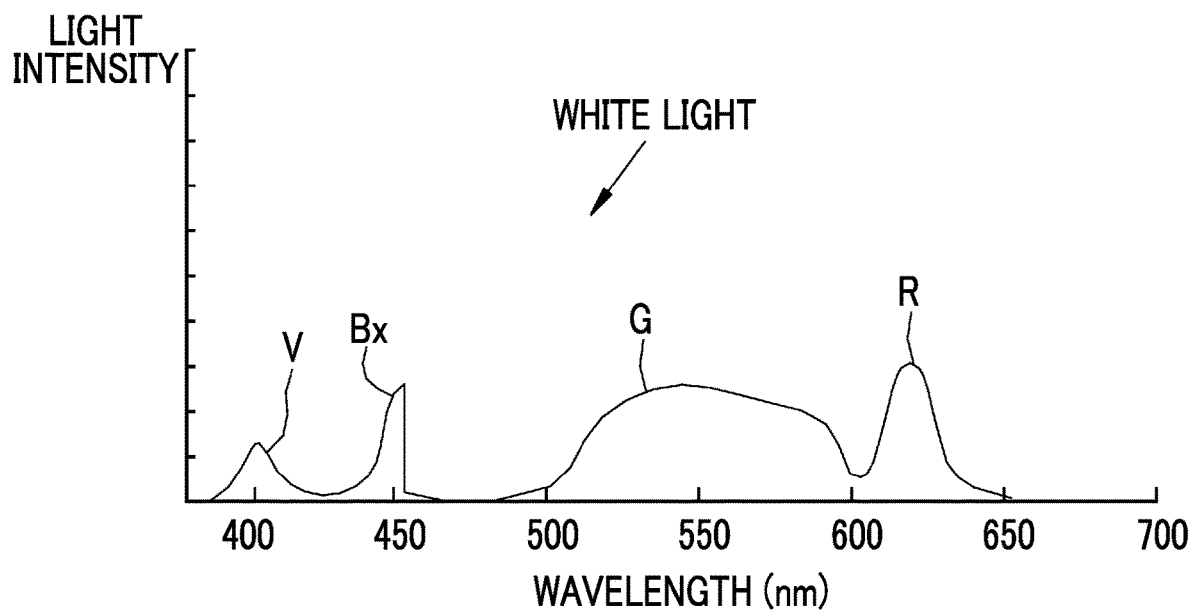
FIG. 19 is a graph illustrating a spectrum of white light obtained by emission of a plurality of LEDs.
Figure 20:
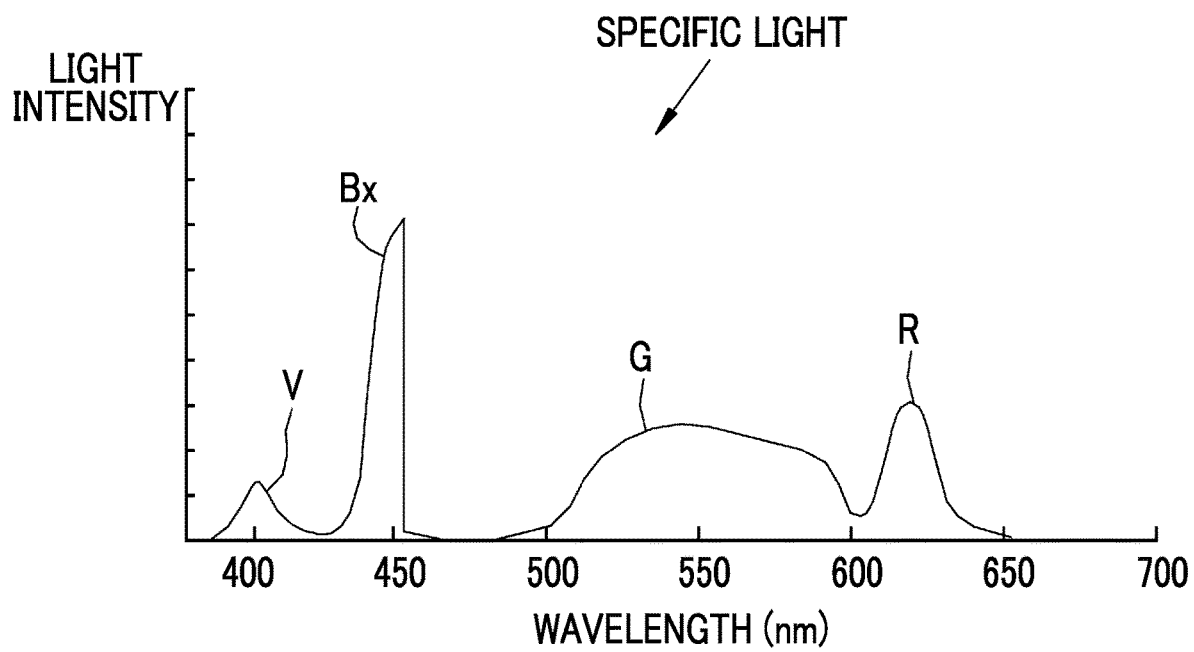
FIG. 20 is a graph illustrating a spectrum of specific light obtained by emission of a plurality of LEDs.

In a case where light in a white-light wavelength range (white light) is emitted, all of the V-LED 20a, the B-LED 20b, the G-LED 20c, and the R-LED 20d are turned on. In this manner, as illustrated in FIG. 19, the light source device 14 emits white light including violet light V, blue light Bx, green light and red light R. Since white light has an intensity of a certain level or greater from the blue-light wavelength rang to the red-light wavelength range, white light is almost white. In a case where specific light having a peak wavelength in a wavelength range of 440±10 nm is emitted as the light in a specific wavelength range (specific light), for example, as illustrated in FIG. 20, specific light in which the light emission amount of blue light Bx is greater than any light emission amount of violet light V, green light and red light R is emitted.

Figure 21:
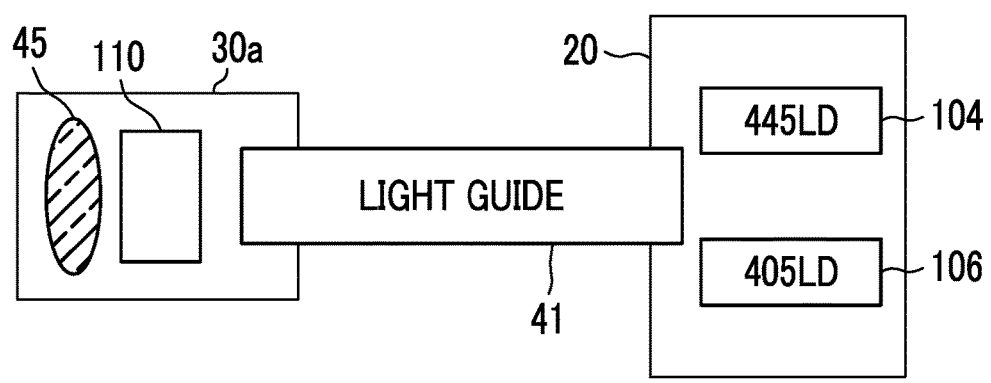
FIG. 21 is a block diagram illustrating a light source unit comprising a laser light source, and a phosphor.

In the embodiment, illumination light may be emitted using the laser light source and a phosphor. In this case, as illustrated in FIG. 21, the light source unit 20 is provided with a blue laser light source (indicated as "445LD", LD indicates a "laser diode") 104 that emits blue laser light having a peak wavelength of 445±10 nm, and a blue-violet laser light source (indicated as "405LD") 106 that emits blue-violet laser light having a peak wavelength of 405±10 nm.

The illumination optical system 30a is provided with a phosphor 110 on which blue laser light or blue-violet laser light is incident from the light guide 41, in addition to the illumination lens 45. The phosphor 110 is excited by blue laser light to emit fluorescence. In addition, some of blue laser light is transmitted without exciting the phosphor 110. Blue-violet laser light is transmitted without exciting the phosphor 110. Light from the phosphor 110 illuminates the body of the observation target via the illumination lens 45.

Figure 22:
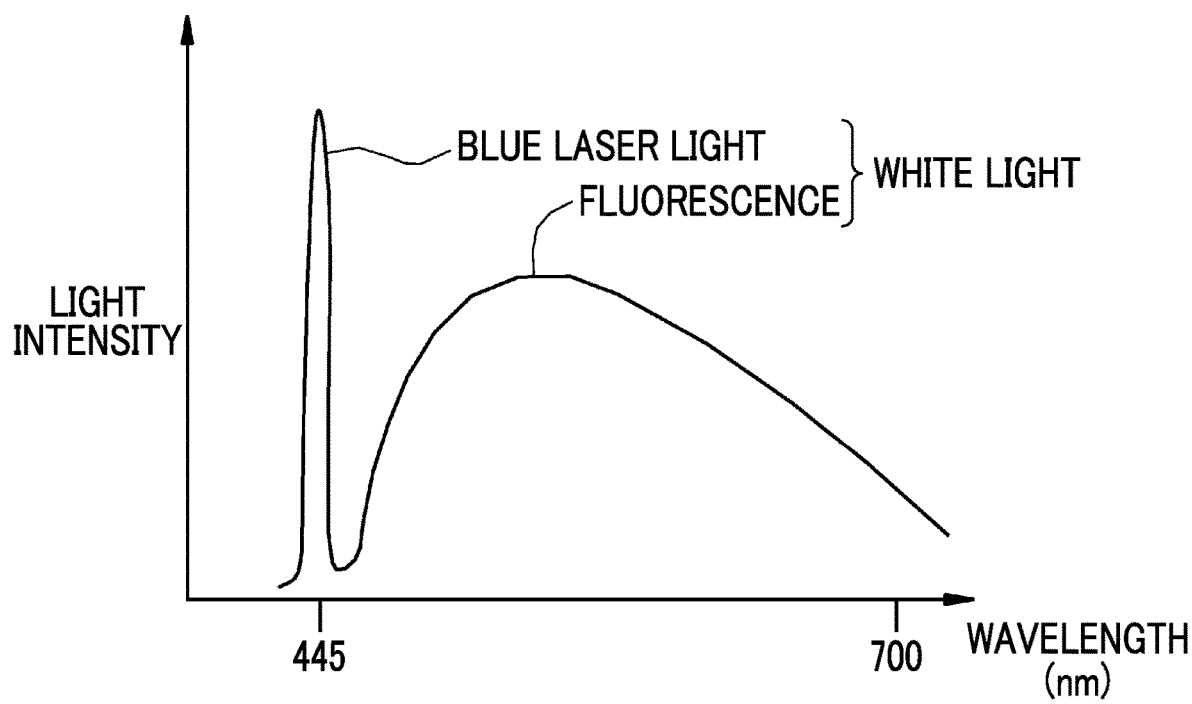
FIG. 22 is a graph illustrating a spectrum of white light emitted using a laser light source and a phosphor.
Figure 23:
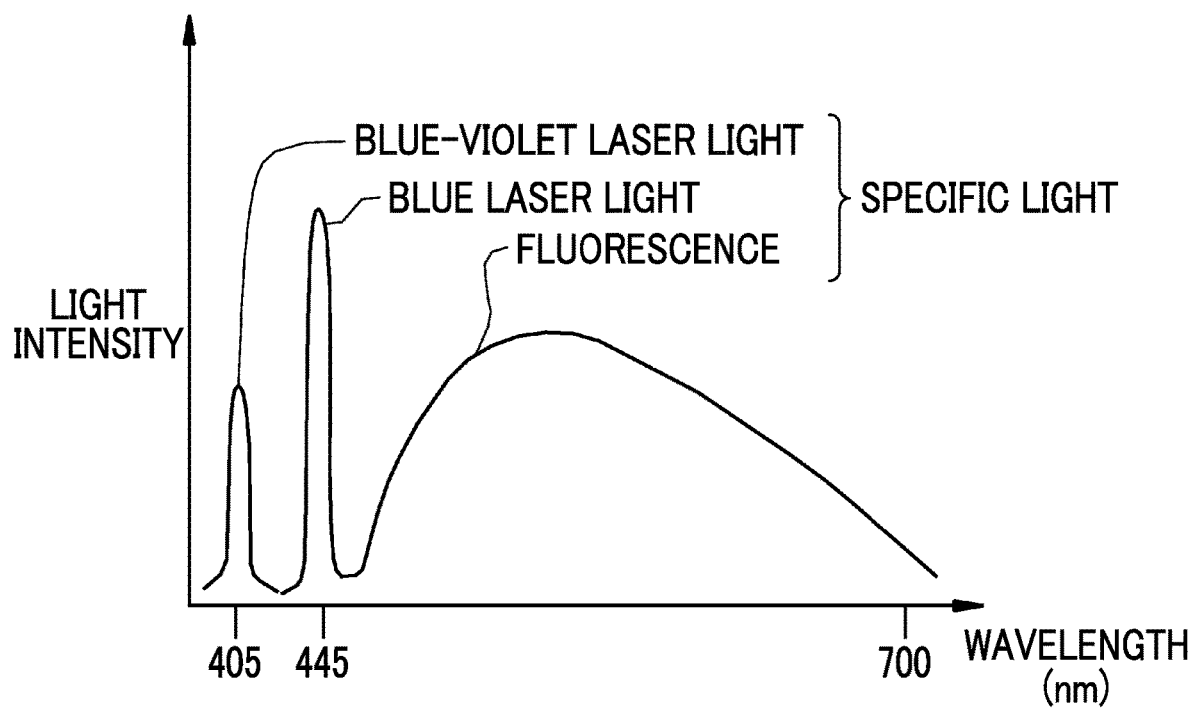
FIG. 23 is a graph illustrating a spectrum of specific light emitted using a laser light source and a phosphor.

Here, in a case where white light is emitted, the blue laser light source 104 is turned on so that blue laser light is mainly incident on the phosphor 110, and thus white light in which blue laser light and fluorescence emitted from the phosphor 110 excited by blue laser light are combined, as illustrated in FIG. 22 is emitted. Meanwhile, in a case where specific light having a peak wavelength in a wavelength range of 440±10 nm is emitted as the light in a specific wavelength range (specific light), the blue laser light source 104 and the blue-violet laser light source 106 are turned on so that both blue-violet laser light and blue laser light are incident on the phosphor 110. In this manner, specific light in which blue-violet laser light, blue laser light, and fluorescence emitted from the phosphor 110 excited by blue laser light are combined, as illustrated in FIG. 23 is emitted.

It is preferable that the half-width of blue laser light or blue-violet laser light is about ±10 nm. As the blue laser light source 104 and the blue-violet laser light source 106, broad area type InGaN laser diodes can be used, and InGaNAs laser diodes and GaNAs laser diodes can also be used. A configuration using a light emitter such as a light emitting diode may be used as the light source.

It is preferable to use the phosphor 110 configured to include a plurality of types of phosphors that absorb some of blue laser light to emit light from green to yellow by excitation (for example, YAG phosphor or phosphor such as BAM ($BaMgAl_{10}O_{17}$)). In a case where a semiconductor light emitting element is used as an excitation light source of the phosphor 110 as in this configuration example, it is possible to obtain high intensity white light with high luminous efficiency, to easily adjust the intensity of white light, and suppress changes in color temperature and chromaticity of white light to be small.

Figure 24:
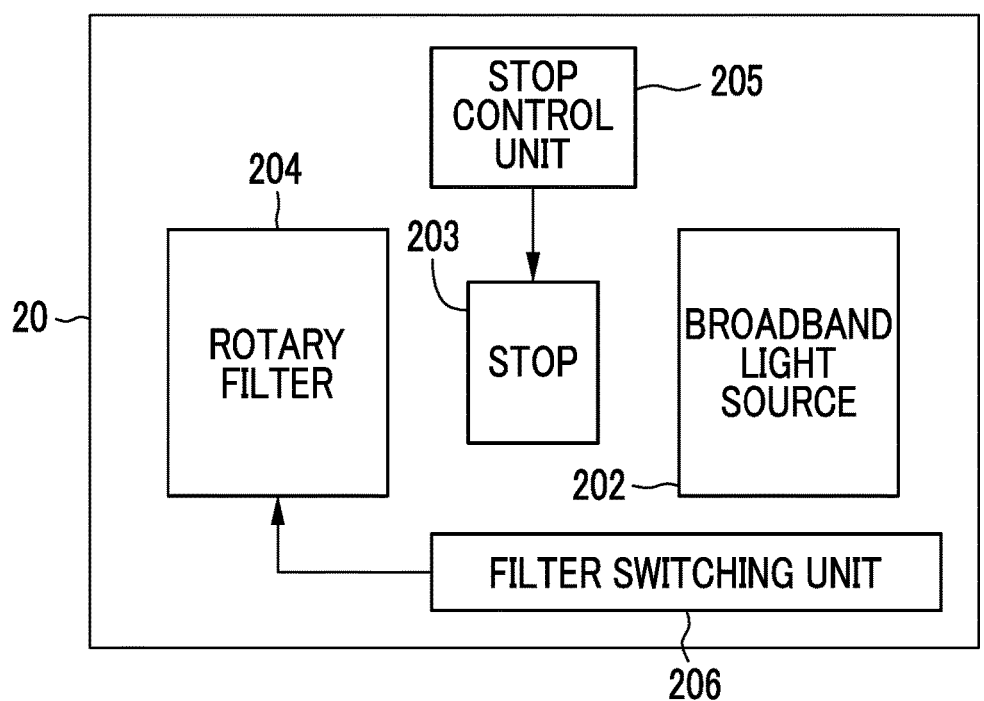
FIG. 24 is a block diagram illustrating a light source unit comprising a broadband light source and a rotary filter.

In the embodiment, illumination light may be emitted using a broadband light source such as a xenon lamp and a rotary filter. In this case, as illustrated in FIG. 24, a broadband light source 202, a rotary filter 204, and a filter switching unit 206 are provided in the light source unit 20. Further, a stop 203 is provided between the broadband light source 202 and the rotary filter 204, and the area of the opening of the stop 203 is adjusted by a stop control unit 205. The stop control unit 205 controls the stop 203 on the basis of dimming signals from the processor device 16.

The broadband light source 202 is a xenon lamp, a white LED, or the like, and emits broadband light having a wavelength range from blue to red. The rotary filter 204 comprises a white light filter 210 provided on the inner side closest to the rotation axis, and a specific light filter 212 provided on the outer side of the white light filter 210 (refer to FIG. 25).

The filter switching unit 206 moves the rotary filter 204 in a radial direction. Specifically, the filter switching unit 206 inserts the white light filter 210 to the light path of broadband light in a case where white light is emitted. The filter switching unit 206 inserts the specific light filter 212 to the light path of broadband light in a case where light in a specific wavelength range (specific light) is emitted.

Figure 25:
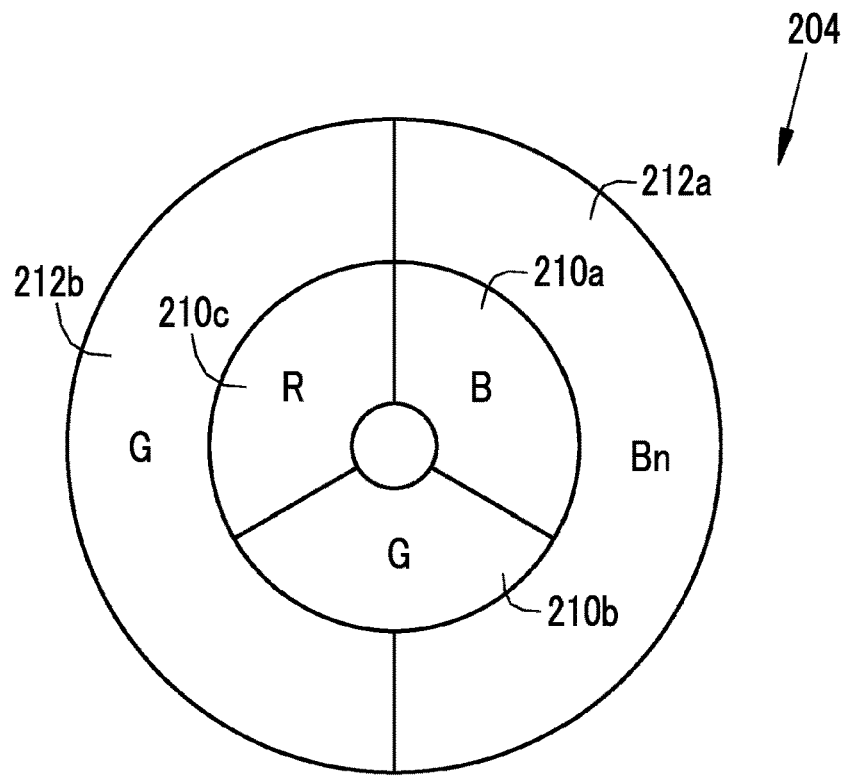
FIG. 25 is a plan view illustrating a rotary filter.

As illustrated in FIG. 25, the white light filter 210 is provided with a B filter 210a, a G filter 210b, and an R filter 210c along the circumferential direction. The B filter 210a transmits broadband blue light B having a wavelength range of 400 nm to 500 nm among broadband light. The G filter 210b transmits green light G among broadband light. The R filter 210c transmits red light R among broadband light. Accordingly, in a case where white light is emitted, as white light, blue light B, green light and red light R are sequentially emitted by the rotation of the rotary filter 204.

The specific light filter 212 is provided with a Bn filter 212a, and a G filter 212b along the circumferential direction. The Bn filter 212a transmits blue narrow-band light Bn having a wavelength range of 400 nm to 450 nm among broadband light. The G filter 212b transmits green light G among broadband light. Accordingly, in a case where specific light is emitted, as specific light, blue narrow-band light Bn and green light G are sequentially emitted toward the observation target by the rotation of the rotary filter 204.

In a case where illumination light is emitted using the broadband light source such as a xenon lamp and the rotary filter, at the time of illumination of white light, the observation target is imaged using a monochrome image sensor each time the observation target is illuminated with blue B, green light and red light R. An image comprising white light components is generated by the B image, the G image, and the R image obtained by imaging the observation target. Further, at the time of illumination of specific light, the observation target is imaged using a monochrome image sensor each time the observation target is illuminated with the blue narrow-band light Bn and green light and an image comprising specific light components is generated by the Bn image and the G image obtained by such imaging.

In the embodiment, the invention is applied to the endoscope system that performs processing on the endoscopic image as one of the medical images. However, the invention can also be applied to a medical image processing system that processes medical images other than the endoscopic image. The invention can also be applied to a diagnosis support apparatus for performing diagnosis support for a user using the medical image. The invention can also be applied to a medical service support apparatus for supporting the medical service, such as a diagnostic report, using the medical image.

Figure 26:
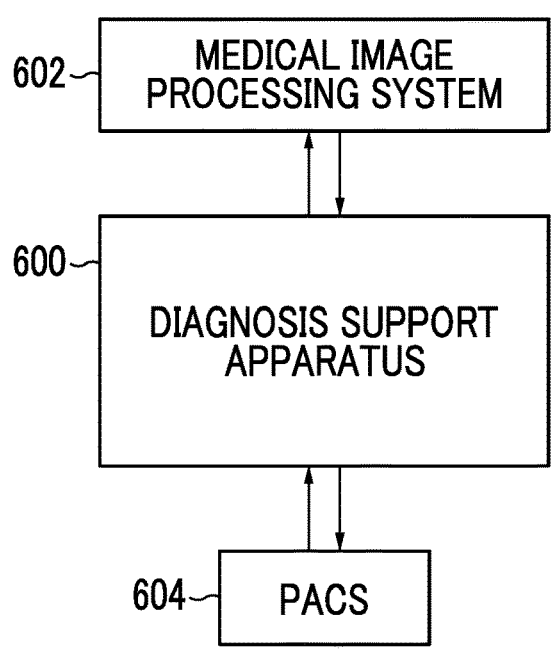
FIG. 26 is a block diagram illustrating a diagnosis support apparatus.
Figure 27:
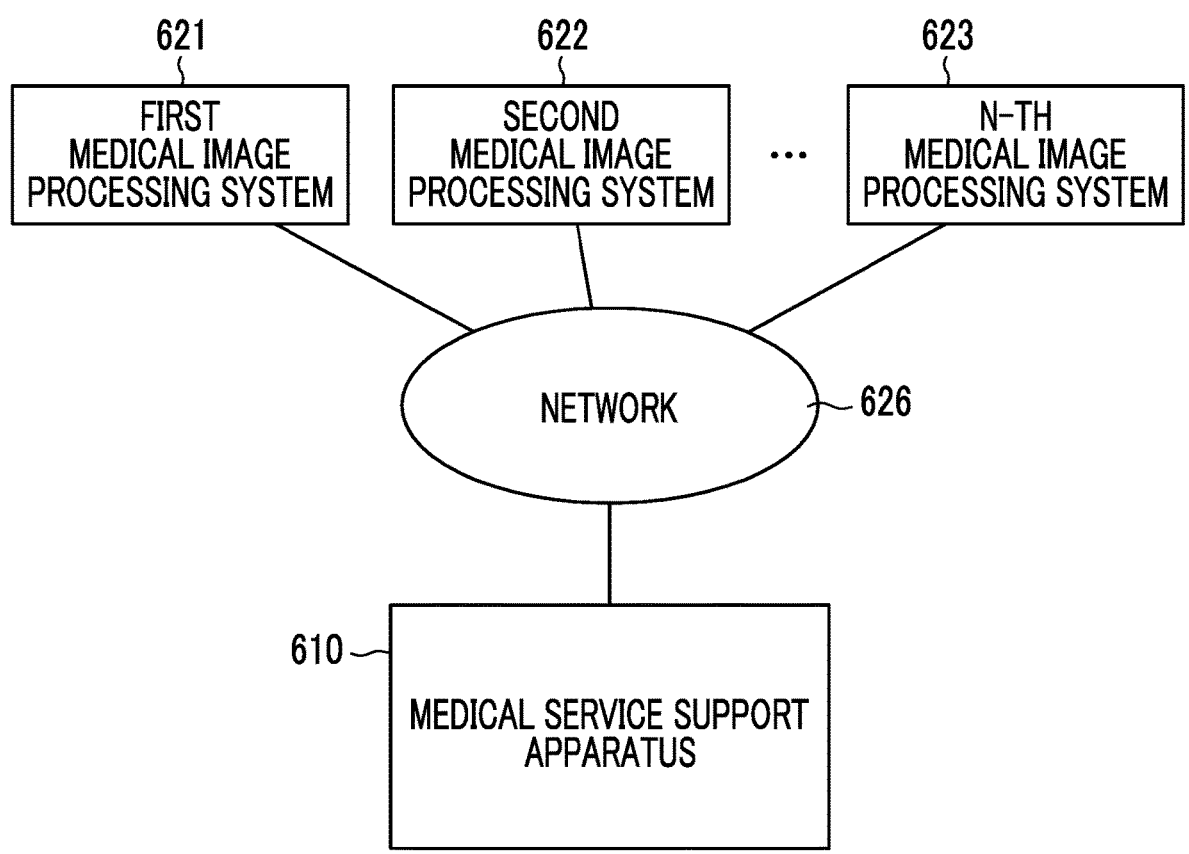
FIG. 27 is a block diagram illustrating a medical service support apparatus.

For example, as illustrated in FIG. 26, a diagnosis support apparatus 600 is used in combination with a modality such as a medical image processing system 602 and a picture archiving and communication system (PACS) 604. As illustrated in FIG. 27, a medical service support apparatus 610 is connected to various inspection devices such as a first medical image processing system 621, a second medical image processing system 622, . . . , and an N-th medical image processing system 623 via any network 626. The medical service support apparatus 610 receives medical images from the first to N-th medical image processing systems 621, 622, . . . , and 623, and supports the medical service on the basis of the received medical images.

In the embodiment, the hardware structure of the processing units executing various kinds of processing, such as the region-of-interest detection unit 70, the diagnosis support information calculation unit 72, the confirmation signal generation unit 77, the region determination instruction generation unit 78, the overlooking determination unit 80, the overlooking notification control unit 82, the gaze image generation unit 92, and the same-target-of-interest determination unit 95 included in the image processing unit 61 is various processors as follows. The various processors include a central processing unit (CPU) as a general-purpose processor executing software (program) and functioning as various processing units, a programmable logic device (PLD) as a processor of which the circuit configuration can be changed after manufacturing such as a field programmable gate array (FPGA), a dedicated electrical circuit as a processor having a circuit configuration designed exclusively for executing various processing, and the like.

One processing unit may be configured by one of the various processors or a combination of the same or different kinds of two or more processors (for example, a combination of a plurality of FPGAs or a combination of a CPU and an FPGA). In addition, a plurality of processing units may be configured by one processor. As an example where a plurality of processing units are configured by one processor, first, there is an aspect where one processor is configured by a combination of one or more CPUs and software as typified by a computer, such as a client or a server, and this processor functions as a plurality of processing units. Second, there is an aspect where a processor fulfilling the functions of the entire system including a plurality of processing units by one integrated circuit (IC) chip as typified by a system on chip (SoC) or the like is used. Thus, various processing units are configured by using one or more of the above-described various processors as hardware structures.

Furthermore, the hardware structures of the various processors are more specifically electrical circuitry in a form in which circuit elements, such as semiconductor elements, are combined.

EXPLANATION OF REFERENCES

- 10: endoscope system
- 12: endoscope
- 12*a*: insertion part
- 12*b*: operation part
- 12*c*: bendable part
- 12*d*: distal end part
- 12*e*: angle knob
- 12*f*: forceps inlet
- 13*a*: zoom operation part
- 13*b*: freeze button
- 13*c*: region approval button
- 14: light source device
- 16: processor device
- 18: monitor
- 19: user interface
- 20: light source unit
- 20*a*: violet light emitting diode (V-LED)
- 20*b*: blue light emitting diode (B-LED)
- 20*c*: green light emitting diode (G-LED)
- 20*d*: red light emitting diode (R-LED)
- 22: light source control unit
- 23: wavelength cut filter
- 30*a*: illumination optical system
- 30*b*: imaging optical system
- 41: light guide
- 45: illumination lens
- 46: objective lens
- 47: zoom lens
- 48: image sensor
- 52: central control unit
- 54: image acquisition unit
- 56: digital signal processor (DSP)
- 58: noise reduction unit
- 59: conversion unit
- 61: image processing unit
- 66: display control unit
- 70: region-of-interest detection unit
- 72: diagnosis support information calculation unit
- 74: main screen
- 74*a*: medical image display unit
- 74*b*: diagnosis support information display unit
- 75: sub screen
- 75*a*: frame (of sub screen)
- 76: static image list screen
- 76*a*: frame (of static image list screen)
- 77: confirmation signal generation unit
- 78: region determination instruction generation unit
- 80: overlooking determination unit
- 82: overlooking notification control unit
- 90: gaze detection unit
- 92: gaze image generation unit
- 95: same-target-of-interest determination unit
- 104: blue laser light source
- 106: blue-violet laser light source
- 110: phosphor
- 202: broadband light source
- 204: rotary filter
- 205: stop control unit
- 206: filter switching unit
- 210: white light filter
- 210*a*: B filter
- 210*b*: G filter
- 210*c*: R filter
- 212: specific light filter
- 212*a*: Bn filter
- 212*b*: G filter
- 600: diagnosis support apparatus
- 602: medical image processing system
- 604: PACS
- 610: medical service support apparatus
- 621: first medical image processing system
- 622: second medical image processing system
- 623: N-th medical image processing system
- 626: network

What is claimed is:

1. A medical image processing system comprising:
   a processor configured to:
   acquire a medical image obtained by imaging an observation target;
   detect a region of interest including a target of interest in the observation target, from the medical image;
   determine whether a user overlooks the target of interest; and
   perform a control relating to an overlooking occurrence notification of the target of interest in a case where it is determined that the target of interest is overlooked; and
   a display that has a first screen which displays a video of the medical image and displays the region of interest, and a second screen which is a screen different from the first screen and displays the region of interest,
   wherein the second screen is displayed at a timing at which the region of interest is detected and displayed on the first screen, and the second screen displays a portion of the medical image that corresponds to the region of interest in the medical image displayed on the first screen,
   wherein the processor calculates an overlooking determination index value for determining an occurrence of the user overlooking the target of interest by respectively multiplying weighting coefficients and conversion coefficients to information of a display time until the region of interest disappears from the first screen after being detected and information of a size of the region of interest and adding results of the multiplications, wherein when the overlooking determination index value exceeds a predetermined overlooking determination threshold value, the processor determines that there is an occurrence of the user overlooking the target of interest.

2. The medical image processing system according to claim 1, wherein in the second screen, a static image of the portion of the medical image including the region of interest and the target of interest is displayed.

3. The medical image processing system according to claim 1, wherein in the second screen, a first alert for prompting the user to confirm the region of interest is displayed.

4. The medical image processing system according to claim 1, wherein the processor is further configured to:
generate a region-of-interest confirmation signal relating to confirmation of the region of interest,
wherein the display displays a second alert indicating that the confirmation of the region of interest by the user is completed in the second screen in a case where the region-of-interest confirmation signal is generated.

5. The medical image processing system according to claim 1, wherein the processor is further configured to:
generate a region determination instruction relating to whether the region of interest is correctly detected,
wherein the display displays a third alert indicating that the region of interest is correctly detected, in the second screen in a case where an instruction indicating that the region of interest is correctly detected is generated as the region determination instruction, and displays a fourth alert indicating that the region of interest is erroneously detected, in the second screen in a case where an instruction indicating that the region of interest is erroneously detected is generated as the region determination instruction.

6. The medical image processing system according to claim 1, wherein the display has a third screen which is a screen different from the first screen and the second screen and displays a list of a plurality of static images, and in the third screen, any one of a first alert for prompting confirmation of the region of interest by the user, a second alert indicating that confirmation of the region of interest by the user is completed, a third alert indicating that the region of interest is correctly detected, or a fourth alert indicating that the region of interest is erroneously detected is displayed.

7. The medical image processing system according to claim 1, further comprising:

a gaze detector that detects a user's gaze directed at the display, wherein the processor further determines overlooking of the target of interest on the basis of an observation time during which the gaze is directed at the region of interest, obtained by the gaze detector.

8. The medical image processing system according to claim 1, wherein the processor performs a control of causing the display to display a message indicating occurrence of the overlooking, as the overlooking occurrence notification.

9. The medical image processing system according to claim 1, wherein the processor is further configured to:
determine whether a first target of interest displayed in the first screen at a first timing and a second target of interest displayed in the first screen at a second timing different from the first timing are the same, and
perform a control of displaying or not displaying the second target of interest in the first screen or the second screen as the region of interest on the basis of a determination result of the processor.

10. The medical image processing system according to claim 9, wherein the processor does not display the second target of interest in the first screen or the second screen as the region of interest in a case where the first target of interest and the second target of interest are the same.

11. The medical image processing system according to claim 1, wherein the display displays the target of interest by assigning an ID number to the target of interest.

12. A diagnosis support apparatus comprising the medical image processing system according to claim 1.

13. A medical service support apparatus comprising the medical image processing system according to claim 1.

14. An endoscope system comprising:
an endoscope that images an observation target;
a processor configured to:
acquire a medical image obtained by imaging an observation target;
detect a region of interest including a target of interest in the observation target, from the medical image;
determine whether a user overlooks the target of interest; and
perform a control relating to an overlooking occurrence notification of the target of interest in a case where it is determined that the target of interest is overlooked; and
a display that has a first screen which displays a video of the medical image and displays the region of interest, and a second screen which is a screen different from the first screen and displays the region of interest,
wherein the second screen is displayed at a timing at which the region of interest is detected and displayed on the first screen, and the second screen displays a portion of the medical image that corresponds to the region of interest in the medical image displayed on the first screen,
wherein the processor calculates an overlooking determination index value for determining an occurrence of the user overlooking the target of interest by respectively multiplying weighting coefficients and conversion coefficients to information of a display time until the region of interest disappears from the first screen after being detected and information of a size of the region of interest and adding results of the multiplications,
wherein when the overlooking determination index value exceeds a predetermined overlooking determination threshold value, the processor determines that there is an occurrence of the user overlooking the target of interest.

* * * * *